(12) United States Patent
Lee et al.

(10) Patent No.: US 7,572,599 B2
(45) Date of Patent: Aug. 11, 2009

(54) METALLOPROTEASE ACTIVATION OF MYOSTATIN, AND METHODS OF MODULATING MYOSTATIN ACTIVITY

(75) Inventors: Se-Jin Lee, Baltimore, MD (US); Alexandra C. McPherron, Baltimore, MD (US); Daniel S. Greenspan, Madison, WI (US); William N. Pappano, Columbia, MD (US); Neil Wolfman, Dover, MA (US); Kathy Tomkinson, Cambridge, MA (US)

(73) Assignees: The Johns Hopkins University School of Medicine, Baltimore, MD (US); Wisconsin Alumni Research Foundation, Madison, WI (US); Wyeth, Madison, NJ (US)

( * ) Notice: Subject to any disclaimer, the term of this patent is extended or adjusted under 35 U.S.C. 154(b) by 268 days.

(21) Appl. No.: 10/665,374

(22) Filed: Sep. 16, 2003

(65) Prior Publication Data

US 2005/0043232 A1    Feb. 24, 2005

Related U.S. Application Data

(60) Provisional application No. 60/486,863, filed on Jul. 10, 2003, provisional application No. 60/439,164, filed on Jan. 9, 2003, provisional application No. 60/411,133, filed on Sep. 16, 2002.

(51) Int. Cl.
*C12Q 1/37*    (2006.01)
(52) U.S. Cl. .............................. 435/23; 435/219; 514/2; 514/12; 514/13; 514/14; 514/15; 530/350; 530/300
(58) Field of Classification Search .................... 435/6; 514/12, 13, 14
See application file for complete search history.

(56) References Cited

U.S. PATENT DOCUMENTS

| 5,994,618 | A | 11/1999 | Lee et al. ..................... 800/18 |
| 2002/0157126 | A1* | 10/2002 | Lee et al. ..................... 800/18 |
| 2003/0104406 | A1 | 6/2003 | Wolfman et al. ............... 435/6 |

FOREIGN PATENT DOCUMENTS

WO    WO 02/09641 A2    2/2002

OTHER PUBLICATIONS

Blader et al., "Cleavage of the BMP-4 antagonist chordin by zebrafish tolloid", *Science*, 278(5345):1937-1940 (Dec. 1997).
Bogdanovich et al., "Functional improvement of dystrophic muscle by myostatin blockade", *Nature*, 420(6914):418-421 (Nov. 2002).
Hill et al., "Regulation of myostatin in vivo by growth and differentiation factor-associated serum protein-1: a novel protein with protease inhibitor and follistatin domains", *Mol. Endocrinol.*, 17(6):1144-1154 (Jun. 2003).

Hill et al., "The myostatin propeptide and the follistatin-related gene are inhibitory binding proteins of myostatin in normal serum", *J. Biol. Chem.*, 277(43):40735-40741 (Oct. 2002).
Kessler et al., "Bone morphogenetic protein-1: the type I procollagen C-proteinase", *Science*, 271(5247):360-362 (Jan. 1996).
Lee et al., "Regulation of myostatin activity and muscle growth", *Proc. Natl. Acad. Sci. USA*, 98(16):9306-9311 (Jul. 2001).
Li et al., "The C-proteinase that processes procollagens to fibrillar collagens is identical to the protein previously identified as bone morphogenic protein-1", *Proc. Natl. Acad. Sci. USA*, 93(10):5127-5130 (May 1996).
Marques et al., "Production of a DPP activity gradient in the early *Drosophila* embryo through the opposing actions of the SOG and TLD proteins", *Cell*, 91(3):417-426 (Oct. 1997).
McPherron et al., "Double muscling in cattle due to mutations in the myostatin gene", *Proc. Natl. Acad. Sci. USA*, 94(23):12457-12461 (Nov. 1997).
McPherron e al., "Regulation of skeletal muscle mass in mice by a new TGF-beta superfamily member", *Nature*, 387(6628):83-90 (May 1997).
Piccolo et al., "Cleavage of Chordin by Xolloid metalloprotease suggests a role for proteolytic processing in the regulation of Spemann organizer activity", *Cell*, 91(3):407-416 (Oct. 1997).
Takahara et al., "Bone morphogenetic protein-1 and a mammalian tolloid homologue (mTld) are encoded by alternatively spliced transcripts which are differentially expressed in some tissues", *J. Biol. Chem.*, 269(51):32572-32578 (Dec. 1994).
Takahara et al., "Characterization of a novel gene product (mammalian tolloid-like) with high sequence similarity to mammalian tolloid/bone morphogenetic protein-1", *Genomics*, 34(2):157-165 (Jun. 1996).
Uzel et al., "Multiple bone morphogenetic protein 1-related mammalian metalloproteinases process pro-lysyl oxidase at the correct physiological site and control lysyl oxidase activation in mouse embryo fibroblast cultures", *J. Biol. Chem.*, 276(25):22537-22543 (Jun. 2001).
Wolfman et al., "Activation of latent myostatin by the BMP-1/tolloid family of metalloproteinases", *Proc. Natl. Acad. Sci. USA*, 100(26):15842-15846 (Dec. 2003).
Wozney et al., "Novel regulators of bone formation: molecular clones and activities", *Science*, 242(4885):1528-1534 (Dec. 1988).

(Continued)

*Primary Examiner*—Nashaat T Nashed
*Assistant Examiner*—Iqbal H Chowdhury
(74) *Attorney, Agent, or Firm*—DLA Piper LLP (US)

(57) ABSTRACT

It has been determined that metalloprotease cleavage of a myostatin pro peptide results in activation of a latent inactive myostatin to an active form. Accordingly, methods of identifying agents that modulate metalloprotease mediated activation of myostatin are provided, as are agents identified using such methods. Also provided are methods of modulating muscle growth in an organism by increasing or decreasing metalloprotease mediated cleavage of a myostatin pro peptide.

9 Claims, 12 Drawing Sheets

OTHER PUBLICATIONS

Blader et al., "Cleavage of the BMP-4 Antagonist Chordin by Zebrafish Tolloid", *Science* 278:1937-1940 (1997).

Bogdanovich et al., "Functional Improvement of Dystrophic Muscle by Myostatin Blockade", *Nature* 420:418-421 (2002).

D'Angelo et al., "Authentic Matrix Vesicles Contain Active Metalloproteases (MMP)", *J. Biol. Chem.* 276:11347-11353 (2001).

Donoghue et al., "Rostrocaudal Gradient of Transgene Expression in Adult Skeletal Muscle", *PNAS* 88:5847-5851 (1991).

Gonzalez-Cadavid et al., "Organization of the Human Myostatin Gene and Expression in Healthy Men and HIV-Infected Men With Muscle Wasting", *PNAS* 95:14938-14943 (1998).

Hill et al., "The Myostatin Propeptide and the Follistatin-Related Gene are Inhibitory Binding Proteins of Myostatin in Normal Serum", *J. Biol. Chem.* 277:40735-40741 (2002).

Hill et al., "Regulation of Myostatin in Vivo by Growth and Differentiation Factor-Associated Serum Protein-1: A Novel Protein with Protease Inhibitor and Follistatin Domains", *Mol. Endocrin.* 17:1144-1154 (2003).

Kessler et al., "Bone Morphogenetic Protein-1: The Type 1 Procollagen C-Proteinase", *Science* 271:360-362 (1996).

Lee et al., "Regulation of Myostatin Activity and Muscle Growth", *PNAS*, 98:9306-9311 (2001).

Lee et al., "Analysis of Site-Directed Mutations in Human Pro-α2 (I) Collagen Which Block Cleavage by the C-Proteinase", *J. Biol. Chem.* 265:21992-21996 (1990).

Li et al., "The C-Proteinase that Processes Procollagens to Fibrillar Collagens is Identical to the Protein Previously Identified as Bone Morphogenic Protein-1", *PNAS* 93:5127-5130 (1996).

Lyons et al., "Proteolytic Activation of Latent Transforming Growth Factor-β from Fibroblast-Conditioned Medium", *J. Cell Biol.* 106:1659-1665 (1988).

Maeda et al., "Activation of Latent Transforming Growth Factor β1 by Stromelysin 1 in Extracts of Growth Plate Chrondrocyte-Derived Matrix Vesicles", *J. Bone Min. Res.* 16:1281-1290 (2001).

Marques et al., "Production of a DPP Activity Gradient in the Early *Drosophilia* Embryo through the Opposing Actions of the SOG and the TLD Proteins", *Cell* 91:417-426 (1997).

McPherron et al., "Double Muscling in Cattle Due to Mutations in the Myostatin Gene", *PNAS* 94:12457-12461 (1997).

McPherron et al., "Regulation of Skeletal Muscle Mass in Mice by a New TGF-β Superfamily Member", *Nature* 387:83-90 (1997).

McPherron et al., "Suppression of Body Fat Accumulation in Myostatin-Deficient Mice", *J. Clin. Invest.* 109:595-601 (2002).

Pappano et al., "Use of *BMP*1/*Tll*1 Doubly Homozygous Null Mice and Proteomics to Identify and Validate In Vivo Substrates of Bone Morphogenetic Protein 1/Tolloid-Like Metalloproteinases", *Mol. Cell Biol.* 23:4428-4438 (2003).

Piccolo et al., "Cleavage of Chordin by Xolloid Metalloprotease Suggests a Role for Proteolytic Processing in the Regulation of Spemann Organizer Activity", *Cell* 91:407-416 (1997).

Sato et al., "Inhibition of Endothelial Cell Movement by Pericytes and Smooth Muscle Cells: Activation of a Latent Transforming Growth Factor -β1-Like Molecule by Plasmin During Co-Culture", *J. Cell Biol.* 109:309-315 (1989).

Scott et al., "Mammalian BMP-1/Tolloid-Related Metalloproteinases, Including Novel Family Member Mammalian Tolloid-Like 2, Have Differential Enzymatic Activities and Distributions of Expression Relevant to Patterning and Skeletogenesis", *Devel. Biol.* 213:283-300 (1999).

Scott et al., "Bone Morphogenetic Protein-1 Processes Probiglycan", *J. Biol. Chem.* 275:30504-30511 (2000).

Sternberg et al., "Identification of Upstream and Intragenic Regulatory Elements that Confer Cell-Type-Restricted and Differentiation-Specific Expression on the Muscle Creatine Kinase Gene", *Mol. Cell Biol.* 8:2896-2909 (1988).

Takahara et al., "Bone Morphogenetic Protein-1 and a Mammalian Tolloid Homologue (mTld) Are Encoded by Alternatively Spliced Transcripts Which Are Differentially Expressed in Some Tissues", *J. Biol. Chem.* 269:32572-32578 (1994).

Takahara et al., "Characterization of a Novel Gene Product (Mammalian Tolloid-like) with High Sequence Similarity to Mammalian Tolloid/Bone Morphogenetic Protein-1", *Genomics* 34:157-165 (1996).

Thies et al., "GDF-8 Propeptide Binds to GDF-8 and Antagonizes Biological Activity by Inhibiting GDF-8 Receptor Binding", *Growth Factors* 18:251-259 (2001).

Uzel et al., "Multiple Bone Morphogenetic Protien 1-Related Mammalian Metalloproteinases Process Pro-Lysyl Oxidase at the Correct Physiological Site and Control Lysyl Oxidase Activation in Mouse Embryo Fibroblast Cultures", *J. Biol. Chem.* 276:22537-22543 (2001).

Yu et al., "Cell Surface-Localized Matrix Metalloproteinase-9 Proteolytically Activates TGF-β and Promotes Tumor Invasion and Angiogenesis", *Genes Dev.* 14:163-176 (2000).

Wagner et al., "Loss of Myostatin Attenuates Severity of Muscular Dystrophy in *mdx* Mice", *Ann. Neurol.* 52:832-836 (2002).

Whittemore et al., "Inhibition of Myostatin in Adult Mice Increases Skeletal Muscle Mass and Strength", *Biochem. Biophys. Res. Comm.* 300:965-971 (2003).

Wozney et al., "Novel Regulators of Bone Formation: Molecular Clones and Activities", *Science* 242:1528-1534 (1988).

Zimmers et al., "Induction of Cachexia in Mice by Systemically Administered Myostatin", *Science* 296:1486-1488 (2002).

Zhu et al., "Dominant Negative Myostatin Produces Hypertrophy without Hyperplasia in Muscle." *FEBS Letters* 474(1):71-75 (2000).

Sequence alignment of a sequence of Lee et al. (SEQ ID No. 2) from U.S. patent No. 6,891,082 with SEQ ID No. 9 from of the U.S. Appl. No. 11/498,498.

* cited by examiner

SEQUENCE LISTING

<160> NUMBER OF SEQ ID NOS: 23

<210> SEQ ID NO 1
<211> LENGTH: 2743
<212> TYPE: DNA
<213> ORGANISM: Homo sapiens
<220> FEATURE:
<221> NAME/KEY: CDS
<222> LOCATION: (59)..(1183)
<223> OTHER INFORMATION:

<400> SEQUENCE: 1

```
aagaaaagta aaggaagaa acaagaacaa gaaaaaagat tatattgatt ttaaaatc           58 atg caa aaa ctg caa ctc tgt gtt tat att tac ctg ttt atg ctg att        106
Met Gln Lys Leu Gln Leu Cys Val Tyr Ile Tyr Leu Phe Met Leu Ile
1               5                   10                  15 gtt gct ggt cca gtg gat cta aat gag aac agt gag caa aaa gaa aat        154
Val Ala Gly Pro Val Asp Leu Asn Glu Asn Ser Glu Gln Lys Glu Asn
            20                  25                  30 gtg gaa aaa gag ggg ctg tgt aat gca tgt act tgg aga caa aac act        202
Val Glu Lys Glu Gly Leu Cys Asn Ala Cys Thr Trp Arg Gln Asn Thr
        35                  40                  45 aaa tct tca aga ata gaa gcc att aag ata caa atc ctc agt aaa ctt        250
Lys Ser Ser Arg Ile Glu Ala Ile Lys Ile Gln Ile Leu Ser Lys Leu
    50                  55                  60 cgt ctg gaa aca gct cct aac atc agc aaa gat gtt ata aga caa ctt        298
Arg Leu Glu Thr Ala Pro Asn Ile Ser Lys Asp Val Ile Arg Gln Leu
65                  70                  75                  80 tta ccc aaa gct cct cca ctc cgg gaa ctg att gat cag tat gat gtc        346
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac        394
Gln Arg Asp Asp Ser Ser Asp Gly Ser Leu Glu Asp Asp Asp Tyr His
            100                 105                 110 gct aca acg gaa aca atc att acc atg cct aca gag tct gat ttt cta        442
Ala Thr Thr Glu Thr Ile Ile Thr Met Pro Thr Glu Ser Asp Phe Leu
        115                 120                 125 atg caa gtg gat gga aaa ccc aaa tgt tgc ttc ttt aaa ttt agc tct        490
Met Gln Val Asp Gly Lys Pro Lys Cys Cys Phe Phe Lys Phe Ser Ser
    130                 135                 140 aaa ata caa tac aat aaa gta gta aag gcc caa cta tgg ata tat ttg        538
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc        586
Arg Pro Val Glu Thr Pro Thr Thr Val Phe Val Gln Ile Leu Arg Leu
                165                 170                 175 atc aaa cct atg aaa gac ggt aca agg tat act gga atc cga tct ctg        634
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg        682
Lys Leu Asp Met Asn Pro Gly Thr Gly Ile Trp Gln Ser Ile Asp Val
        195                 200                 205 aag aca gtg ttg caa aat tgg ctc aaa caa cct gaa tcc aac tta ggc        730
Lys Thr Val Leu Gln Asn Trp Leu Lys Gln Pro Glu Ser Asn Leu Gly
    210                 215                 220 att gaa ata aaa gct tta gat gag aat ggt cat gat ctt gct gta acc        778
Ile Glu Ile Lys Ala Leu Asp Glu Asn Gly His Asp Leu Ala Val Thr
225                 230                 235                 240 ttc cca gga cca gga gaa gat ggg ctg aat ccg ttt tta gag gtc aag        826
```

```
                Phe Pro Gly Pro Gly Glu Asp Gly Leu Asn Pro Phe Leu Glu Val Lys
                            245                 250                 255 gta aca gac aca cca aaa aga tcc aga agg gat ttt ggt ctt gac tgt          874
Val Thr Asp Thr Pro Lys Arg Ser Arg Arg Asp Phe Gly Leu Asp Cys
            260                 265                 270 gat gag cac tca aca gaa tca cga tgc tgt cgt tac cct cta act gtg          922
Asp Glu His Ser Thr Glu Ser Arg Cys Cys Arg Tyr Pro Leu Thr Val
                275                 280                 285 gat ttt gaa gct ttt gga tgg gat tgg att atc gct cct aaa aga tat          970
Asp Phe Glu Ala Phe Gly Trp Asp Trp Ile Ile Ala Pro Lys Arg Tyr
            290                 295                 300 aag gcc aat tac tgc tct gga gag tgt gaa ttt gta ttt tta caa aaa         1018
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca         1066
Tyr Pro His Thr His Leu Val His Gln Ala Asn Pro Arg Gly Ser Ala
                325                 330                 335 ggc cct tgc tgt act ccc aca aag atg tct cca att aat atg cta tat         1114
Gly Pro Cys Cys Thr Pro Thr Lys Met Ser Pro Ile Asn Met Leu Tyr
            340                 345                 350 ttt aat ggc aaa gaa caa ata ata tat ggg aaa att cca gcg atg gta         1162
Phe Asn Gly Lys Glu Gln Ile Ile Tyr Gly Lys Ile Pro Ala Met Val
                355                 360                 365 gta gac cgc tgt ggg tgc tca tgagatttat attaagcgtt cataacttcc            1213
Val Asp Arg Cys Gly Cys Ser
            370                 375 taaaacatgg aaggttttcc cctcaacaat tttgaagctg tgaaattaag taccacaggc       1273
tataggccta gagtatgcta cagtcactta agcataagct acagtatgta aactaaaagg       1333
gggaatatat gcaatggttg gcatttaacc atccaaacaa atcatacaag aaagttttat       1393
gatttccaga gttttgagc tagaaggaga tcaaattaca tttatgttcc tatatattac        1453
aacatcggcg aggaaatgaa agcgattctc cttgagttct gatgaattaa aggagtatgc       1513
tttaaagtct atttctttaa agttttgttt aatatttaca gaaaaatcca catacagtat       1573
tggtaaaatg caggattgtt ataccatc attcgaatca tccttaaaca cttgaattta        1633
tattgtatgg tagtatactt ggtaagataa aattccacaa aaatagggat ggtgcagcat       1693
atgcaatttc cattcctatt ataattgaca cagtacatta acaatccatg ccaacggtgc      1753
taatacgata ggctgaatgt ctgaggctac caggtttatc acataaaaaa cattcagtaa       1813
aatagtaagt ttctcttttc ttcaggtgca ttttcctaca cctccaaatg aggaatggat      1873
tttctttaat gtaagaagaa tcattttct agaggttggc tttcaattct gtagcatact       1933
tggagaaact gcattatctt aaaaggcagt caaatggtgt ttgtttttat caaaatgtca      1993
aaataacata cttggagaag tatgtaattt tgtctttgga aaattacaac actgcctttg      2053
caacactgca gttttatgg taaaataata gaaatgatcg actctatcaa tattgtataa      2113
aaagactgaa acaatgcatt tatataatat gtatacaata ttgttttgta aataagtgtc     2173
tcctttttta tttactttgg tatatttta cactaaggac atttcaaatt aagtactaag      2233
gcacaaagac atgtcatgca tcacagaaaa gcaactactt atatttcaga gcaaattagc    2293
agattaaata gtggtcttaa aactccatat gttaatgatt agatggttat attcaatca     2353 ttttatattt ttttacatga ttaacattca cttatggatt catgatggct gtataaagtg   2413
aatttgaaat ttcaatggtt tactgtcatt gtgtttaaat ctcaacgttc cattatttta  2473
atacttgcaa aaacattact aagtatacca aaataattga ctctattatc tgaaatgaag   2533
```

-continued

```
aataaactga tgctatctca acaataactg ttacttttat tttataattt gataatgaat    2593
atatttctgc atttatttac ttctgttttg taaattggga ttttgttaat caaatttatt    2653
gtactatgac taaatgaaat tatttcttac atctaatttg tagaaacagt ataagttata    2713
ttaaagtgtt ttcacatttt tttgaaagac                                     2743

<210> SEQ ID NO 2
<211> LENGTH: 375
<212> TYPE: PRT
<213> ORGANISM: Homo sapiens

<400> SEQUENCE: 2

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335
```

```
Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
            355                 360                 365

Val Asp Arg Cys Gly Cys Ser
    370                 375

<210> SEQ ID NO 3
<211> LENGTH: 1128
<212> TYPE: DNA
<213> ORGANISM: Bovine
<220> FEATURE:
<221> NAME/KEY: CDS
<222> LOCATION: (1)..(1125)
<223> OTHER INFORMATION:

<400> SEQUENCE: 3
```

| | | |
|---|---|---|
| atg caa aaa ctg caa atc tct gtt tat att tac cta ttt atg ctg att<br>Met Gln Lys Leu Gln Ile Ser Val Tyr Ile Tyr Leu Phe Met Leu Ile<br>1               5                   10                  15 | | 48 |
| gtt gct ggc cca gtg gat ctg aat gag aac agc gag cag aag gaa aat<br>Val Ala Gly Pro Val Asp Leu Asn Glu Asn Ser Glu Gln Lys Glu Asn<br>            20                  25                  30 | | 96 |
| gtg gaa aaa gag ggg ctg tgt aat gca tgt ttg tgg agg gaa aac act<br>Val Glu Lys Glu Gly Leu Cys Asn Ala Cys Leu Trp Arg Glu Asn Thr<br>        35                  40                  45 | | 144 |
| aca tcg tca aga cta gaa gcc ata aaa atc caa atc ctc agt aaa ctt<br>Thr Ser Ser Arg Leu Glu Ala Ile Lys Ile Gln Ile Leu Ser Lys Leu<br>    50                  55                  60 | | 192 |
| cgc ctg gaa aca gct cct aac atc agc aaa gat gct atc aga caa ctt<br>Arg Leu Glu Thr Ala Pro Asn Ile Ser Lys Asp Ala Ile Arg Gln Leu<br>65                  70                  75                  80 | | 240 |
| ttg ccc aag gct cct cca ctc ctg gaa ctg att gat cag ttc gat gtc<br>Leu Pro Lys Ala Pro Pro Leu Leu Glu Leu Ile Asp Gln Phe Asp Val<br>                85                  90                  95 | | 288 |
| cag aga gat gcc agc agt gac ggc tcc ttg gaa gac gat gac tac cac<br>Gln Arg Asp Ala Ser Ser Asp Gly Ser Leu Glu Asp Asp Asp Tyr His<br>            100                 105                 110 | | 336 |
| gcc agg acg gaa acg gtc att acc atg ccc acg gag tct gat ctt cta<br>Ala Arg Thr Glu Thr Val Ile Thr Met Pro Thr Glu Ser Asp Leu Leu<br>        115                 120                 125 | | 384 |
| acg caa gtg gaa gga aaa ccc aaa tgt tgc ttc ttt aaa ttt agc tct<br>Thr Gln Val Glu Gly Lys Pro Lys Cys Cys Phe Phe Lys Phe Ser Ser<br>    130                 135                 140 | | 432 |
| aag ata caa tac aat aaa cta gta aag gcc caa ctg tgg ata tat ctg<br>Lys Ile Gln Tyr Asn Lys Leu Val Lys Ala Gln Leu Trp Ile Tyr Leu<br>145                 150                 155                 160 | | 480 |
| agg cct gtc aag act cct gcg aca gtg ttt gtg caa atc ctg aga ctc<br>Arg Pro Val Lys Thr Pro Ala Thr Val Phe Val Gln Ile Leu Arg Leu<br>                165                 170                 175 | | 528 |
| atc aaa ccc atg aaa gac ggt aca agg tat act gga atc cga tct ctg<br>Ile Lys Pro Met Lys Asp Gly Thr Arg Tyr Thr Gly Ile Arg Ser Leu<br>            180                 185                 190 | | 576 |
| aaa ctt gac atg aac cca ggc act ggt att tgg cag agc att gat gtg<br>Lys Leu Asp Met Asn Pro Gly Thr Gly Ile Trp Gln Ser Ile Asp Val<br>        195                 200                 205 | | 624 |
| aag aca gtg ttg cag aac tgg ctc aaa caa cct gaa tcc aac tta ggc<br>Lys Thr Val Leu Gln Asn Trp Leu Lys Gln Pro Glu Ser Asn Leu Gly<br>    210                 215                 220 | | 672 |
| att gaa atc aaa gct tta gat gag aat ggc cat gat ctt gct gta acc<br>Ile Glu Ile Lys Ala Leu Asp Glu Asn Gly His Asp Leu Ala Val Thr | | 720 |

-continued

```
                  225                 230                 235                 240
ttc cca gaa cca gga gaa gat gga ctg act ccc ttt tta gaa gtc aag      768
Phe Pro Glu Pro Gly Glu Asp Gly Leu Thr Pro Phe Leu Glu Val Lys
                      245                 250                 255 gta aca gac aca cca aaa aga tct agg aga gat ttt ggg ctt gat tgt      816
Val Thr Asp Thr Pro Lys Arg Ser Arg Arg Asp Phe Gly Leu Asp Cys
                260                 265                 270 gat gaa cac tcc aca gaa tct cga tgc tgt cgt tac cct cta act gtg      864
Asp Glu His Ser Thr Glu Ser Arg Cys Cys Arg Tyr Pro Leu Thr Val
            275                 280                 285 gat ttt gaa gct ttt gga tgg gat tgg att att gca cct aaa aga tat      912
Asp Phe Glu Ala Phe Gly Trp Asp Trp Ile Ile Ala Pro Lys Arg Tyr
        290                 295                 300 aag gcc aat tac tgc tct gga gaa tgt gaa ttt gta ttt ttg caa aag      960
Lys Ala Asn Tyr Cys Ser Gly Glu Cys Glu Phe Val Phe Leu Gln Lys
305                 310                 315                 320 tat cct cat acc cat ctt gtg cac caa gca aac ccc aga ggt tca gcc     1008
Tyr Pro His Thr His Leu Val His Gln Ala Asn Pro Arg Gly Ser Ala
                    325                 330                 335 ggc ccc tgc tgt act cct aca aag atg tct cca att aat atg cta tat     1056
Gly Pro Cys Cys Thr Pro Thr Lys Met Ser Pro Ile Asn Met Leu Tyr
                340                 345                 350 ttt aat ggc gaa gga caa ata ata tac ggg aag att cca gcc atg gta     1104
Phe Asn Gly Glu Gly Gln Ile Ile Tyr Gly Lys Ile Pro Ala Met Val
            355                 360                 365 gta gat cgc tgt ggg tgt tca tga                                     1128
Val Asp Arg Cys Gly Cys Ser
        370                 375

<210> SEQ ID NO 4
<211> LENGTH: 375
<212> TYPE: PRT
<213> ORGANISM: Bovine

<400> SEQUENCE: 4

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175
```

```
Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Glu Gly Gln Ile Ile Tyr Gly Lys Ile Pro Ala Met Val
        355                 360                 365

Val Asp Arg Cys Gly Cys Ser
370                 375

<210> SEQ ID NO 5
<211> LENGTH: 1128
<212> TYPE: DNA
<213> ORGANISM: Gallus gallus
<220> FEATURE:
<221> NAME/KEY: CDS
<222> LOCATION: (1)..(1125)
<223> OTHER INFORMATION:

<400> SEQUENCE: 5 atg caa aag ctg gca gtc tat gtt tat att tac ctg ttc atg cag atc      48
Met Gln Lys Leu Ala Val Tyr Val Tyr Ile Tyr Leu Phe Met Gln Ile
1               5                   10                  15 gcg gtt gat ccg gtg gct ctg gat ggc agt agt cag ccc aca gag aac      96
Ala Val Asp Pro Val Ala Leu Asp Gly Ser Ser Gln Pro Thr Glu Asn
                20                  25                  30 gct gaa aaa gac gga ctg tgc aat gct tgt acg tgg aga cag aat aca     144
Ala Glu Lys Asp Gly Leu Cys Asn Ala Cys Thr Trp Arg Gln Asn Thr
            35                  40                  45 aaa tcc tcc aga ata gaa gcc ata aaa att caa atc ctc agc aaa ctg     192
Lys Ser Ser Arg Ile Glu Ala Ile Lys Ile Gln Ile Leu Ser Lys Leu
        50                  55                  60 cgc ctg gaa caa gca cct aac att agc agg gac gtt att aag cag ctt     240
Arg Leu Glu Gln Ala Pro Asn Ile Ser Arg Asp Val Ile Lys Gln Leu
65                  70                  75                  80 tta ccc aaa gct cct cca ctg cag gaa ctg att gat cag tat gat gtc     288
Leu Pro Lys Ala Pro Pro Leu Gln Glu Leu Ile Asp Gln Tyr Asp Val
                85                  90                  95 cag agg gac gac agt agc gat ggc tct ttg gaa gac gat gac tat cat     336
Gln Arg Asp Asp Ser Ser Asp Gly Ser Leu Glu Asp Asp Asp Tyr His
                100                 105                 110
```

| | | |
|---|---|---|
| gcc aca acc gag acg att atc aca atg cct acg gag tct gat ttt ctt<br>Ala Thr Thr Glu Thr Ile Ile Thr Met Pro Thr Glu Ser Asp Phe Leu<br>        115                    120                    125 | 384 |
| gta caa atg gag gga aaa cca aaa tgt tgc ttc ttt aag ttt agc tct<br>Val Gln Met Glu Gly Lys Pro Lys Cys Cys Phe Phe Lys Phe Ser Ser<br>130                    135                    140 | 432 |
| aaa ata caa tat aac aaa gta gta aag gca caa tta tgg ata tac ttg<br>Lys Ile Gln Tyr Asn Lys Val Val Lys Ala Gln Leu Trp Ile Tyr Leu<br>145                    150                    155                    160 | 480 |
| agg caa gtc caa aaa cct aca acg gtg ttt gtg cag atc ctg aga ctc<br>Arg Gln Val Gln Lys Pro Thr Thr Val Phe Val Gln Ile Leu Arg Leu<br>        165                    170                    175 | 528 |
| att aag ccc atg aaa gac ggt aca aga tat act gga att cga tct ttg<br>Ile Lys Pro Met Lys Asp Gly Thr Arg Tyr Thr Gly Ile Arg Ser Leu<br>            180                    185                    190 | 576 |
| aaa ctt gac atg aac cca ggc act ggt atc tgg cag agt att gat gtg<br>Lys Leu Asp Met Asn Pro Gly Thr Gly Ile Trp Gln Ser Ile Asp Val<br>              195                    200                    205 | 624 |
| aag aca gtg ctg caa aat tgg ctc aaa cag cct gaa tcc aat tta ggc<br>Lys Thr Val Leu Gln Asn Trp Leu Lys Gln Pro Glu Ser Asn Leu Gly<br>210                    215                    220 | 672 |
| atc gaa ata aaa gct ttt gat gag act gga cga gat ctt gct gtc aca<br>Ile Glu Ile Lys Ala Phe Asp Glu Thr Gly Arg Asp Leu Ala Val Thr<br>225                    230                    235                    240 | 720 |
| ttc cca gga cca gga gaa gat gga ttg aac cca ttt tta gag gtc aga<br>Phe Pro Gly Pro Gly Glu Asp Gly Leu Asn Pro Phe Leu Glu Val Arg<br>                  245                    250                    255 | 768 |
| gtt aca gac aca ccg aaa cgg tcc cgc aga gat ttt ggc ctt gac tgt<br>Val Thr Asp Thr Pro Lys Arg Ser Arg Arg Asp Phe Gly Leu Asp Cys<br>                    260                    265                    270 | 816 |
| gat gag cac tca acg gaa tcc cga tgt tgt cgc tac ccg ctg aca gtg<br>Asp Glu His Ser Thr Glu Ser Arg Cys Cys Arg Tyr Pro Leu Thr Val<br>                        275                    280                    285 | 864 |
| gat ttc gaa gct ttt gga tgg gac tgg att ata gca cct aaa aga tac<br>Asp Phe Glu Ala Phe Gly Trp Asp Trp Ile Ile Ala Pro Lys Arg Tyr<br>290                    295                    300 | 912 |
| aaa gcc aat tac tgc tcc gga gaa tgc gaa ttt gtg ttt cta cag aaa<br>Lys Ala Asn Tyr Cys Ser Gly Glu Cys Glu Phe Val Phe Leu Gln Lys<br>305                    310                    315                    320 | 960 |
| tac ccg cac act cac ctg gta cac caa gca aat ccc aga ggc tca gca<br>Tyr Pro His Thr His Leu Val His Gln Ala Asn Pro Arg Gly Ser Ala<br>                        325                    330                    335 | 1008 |
| ggc cct tgc tgc aca ccc acc aag atg tcc cct ata aac atg ctg tat<br>Gly Pro Cys Cys Thr Pro Thr Lys Met Ser Pro Ile Asn Met Leu Tyr<br>                            340                    345                    350 | 1056 |
| ttc aat gga aaa gaa caa ata ata tat gga aag ata cca gcc atg gtt<br>Phe Asn Gly Lys Glu Gln Ile Ile Tyr Gly Lys Ile Pro Ala Met Val<br>                              355                    360                    365 | 1104 |
| gta gat cgt tgc ggg tgc tca tga<br>Val Asp Arg Cys Gly Cys Ser<br>        370                    375 | 1128 |

```
<210> SEQ ID NO 6
<211> LENGTH: 375
<212> TYPE: PRT
<213> ORGANISM: Gallus gallus

<400> SEQUENCE: 6
```

Met Gln Lys Leu Ala Val Tyr Val Tyr Ile Tyr Leu Phe Met Gln Ile
1                 5                    10                    15

```
Ala Val Asp Pro Val Ala Leu Asp Gly Ser Ser Gln Pro Thr Glu Asn
             20                  25                  30

Ala Glu Lys Asp Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
 50                  55                  60

Arg Leu Glu Gln Ala Pro Asn Ile Ser Arg Asp Val Ile Lys Gln Leu
 65                  70                  75                  80

Leu Pro Lys Ala Pro Pro Leu Gln Glu Leu Ile Asp Gln Tyr Asp Val
                 85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Val Gln Met Glu Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Phe Asp Glu Thr Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
370                 375

<210> SEQ ID NO 7
<211> LENGTH: 1125
<212> TYPE: DNA
<213> ORGANISM: Danio rerio
<220> FEATURE:
<221> NAME/KEY: CDS
<222> LOCATION: (1)..(1122)
<223> OTHER INFORMATION:
```

<400> SEQUENCE: 7

```
atg cat ttt aca cag gtt tta att tct cta agt gta tta att gca tgt      48
Met His Phe Thr Gln Val Leu Ile Ser Leu Ser Val Leu Ile Ala Cys
 1               5                  10                  15 ggt cca gtg ggt tat gga gat ata acg gcg cac cag cag cct tcc aca      96
Gly Pro Val Gly Tyr Gly Asp Ile Thr Ala His Gln Gln Pro Ser Thr
             20                  25                  30 gcc acg gag gaa agc gag ctg tgt tcc aca tgt gag ttc aga caa cac     144
Ala Thr Glu Glu Ser Glu Leu Cys Ser Thr Cys Glu Phe Arg Gln His
         35                  40                  45 agc aag ctg atg aga ctg cat gcc atc aag tcc caa att ctt agc aaa     192
Ser Lys Leu Met Arg Leu His Ala Ile Lys Ser Gln Ile Leu Ser Lys
     50                  55                  60 ctc cga ctc aag cag gct cca aac atc agc cgg gac gtg gtc aag cag     240
Leu Arg Leu Lys Gln Ala Pro Asn Ile Ser Arg Asp Val Val Lys Gln
 65                  70                  75                  80 ctg tta ccc aaa gca ccg cct ttg caa caa ctt ctg gat cag tac gat     288
Leu Leu Pro Lys Ala Pro Pro Leu Gln Gln Leu Leu Asp Gln Tyr Asp
                 85                  90                  95 gtt tta gga gat gac agt aag gat gga gct gtg gaa gag gac gat gaa     336
Val Leu Gly Asp Asp Ser Lys Asp Gly Ala Val Glu Glu Asp Asp Glu
            100                 105                 110 cat gcc acc aca gag acc atc atg acc atg gcc aca gaa cct gac ccc     384
His Ala Thr Thr Glu Thr Ile Met Thr Met Ala Thr Glu Pro Asp Pro
        115                 120                 125 att gtt caa gta gat cgg aaa ccg aag tgt tgc ttt ttc tcc ttc agt     432
Ile Val Gln Val Asp Arg Lys Pro Lys Cys Cys Phe Phe Ser Phe Ser
    130                 135                 140 ccg aag atc caa gcg aac cgg atc gta aga gcg cag ctc tgg gtt cat     480
Pro Lys Ile Gln Ala Asn Arg Ile Val Arg Ala Gln Leu Trp Val His
145                 150                 155                 160 ctg aga ccg gcg gag gag gcg acc acc gtc ttc tta cag ata tct cgg     528
Leu Arg Pro Ala Glu Glu Ala Thr Thr Val Phe Leu Gln Ile Ser Arg
                165                 170                 175 ctg atg ccc gtt aag gac gga gga aga cac cga ata cga tcc ctg aaa     576
Leu Met Pro Val Lys Asp Gly Gly Arg His Arg Ile Arg Ser Leu Lys
            180                 185                 190 atc gac gtg aac gca gga gtc acg tct tgg cag agt ata gac gta aag     624
Ile Asp Val Asn Ala Gly Val Thr Ser Trp Gln Ser Ile Asp Val Lys
        195                 200                 205 cag gtg ctc acg gtg tgg tta aaa caa ccg gag acc aac cga ggc atc     672
Gln Val Leu Thr Val Trp Leu Lys Gln Pro Glu Thr Asn Arg Gly Ile
    210                 215                 220 gag att aac gca tat gac gcg aag gga aac gac ttg gcc gtc act tca     720
Glu Ile Asn Ala Tyr Asp Ala Lys Gly Asn Asp Leu Ala Val Thr Ser
225                 230                 235                 240 acc gag act ggg gag gat gga ctg ctc ccc ttt atg gag gtg aaa ata     768
Thr Glu Thr Gly Glu Asp Gly Leu Leu Pro Phe Met Glu Val Lys Ile
                245                 250                 255 tca gag ggc cca aaa cga atc cgg agg gac tcc gga ctg gac tgc gat     816
Ser Glu Gly Pro Lys Arg Ile Arg Arg Asp Ser Gly Leu Asp Cys Asp
            260                 265                 270 gag aat tcc tca gag tct cgc tgc tgc agg tac cct ctc act gtg gac     864
Glu Asn Ser Ser Glu Ser Arg Cys Cys Arg Tyr Pro Leu Thr Val Asp
        275                 280                 285 ttc gag gac ttt ggc tgg gac tgg att att gct cca aaa cgc tat aag     912
Phe Glu Asp Phe Gly Trp Asp Trp Ile Ile Ala Pro Lys Arg Tyr Lys
    290                 295                 300 gcg aat tac tgt tca gga gaa tgc gac tac atg tac ctg cag aag tat     960
Ala Asn Tyr Cys Ser Gly Glu Cys Asp Tyr Met Tyr Leu Gln Lys Tyr
```

```
Ala Asn Tyr Cys Ser Gly Glu Cys Asp Tyr Met Tyr Leu Gln Lys Tyr
305                 310                 315                 320 ccc cac acc cat ctg gtg aac aag gcc agt ccg aga gga acg gct ggg    1008
Pro His Thr His Leu Val Asn Lys Ala Ser Pro Arg Gly Thr Ala Gly
                325                 330                 335 ccc tgc tgc act ccc acc aag atg tct ccc atc aac atg ctt tac ttt    1056
Pro Cys Cys Thr Pro Thr Lys Met Ser Pro Ile Asn Met Leu Tyr Phe
            340                 345                 350 aac ggc aaa gag cag atc atc tac ggc aag atc cct tcg atg gta gta    1104
Asn Gly Lys Glu Gln Ile Ile Tyr Gly Lys Ile Pro Ser Met Val Val
        355                 360                 365 gac cgc tgt ggc tgc tca tga                                        1125
Asp Arg Cys Gly Cys Ser
    370

<210> SEQ ID NO 8
<211> LENGTH: 374
<212> TYPE: PRT
<213> ORGANISM: Danio rerio

<400> SEQUENCE: 8

Met His Phe Thr Gln Val Leu Ile Ser Leu Ser Val Leu Ile Ala Cys
1               5                   10                  15

Gly Pro Val Gly Tyr Gly Asp Ile Thr Ala His Gln Gln Pro Ser Thr
            20                  25                  30

Ala Thr Glu Glu Ser Glu Leu Cys Ser Thr Cys Glu Phe Arg Gln His
        35                  40                  45

Ser Lys Leu Met Arg Leu His Ala Ile Lys Ser Gln Ile Leu Ser Lys
    50                  55                  60

Leu Arg Leu Lys Gln Ala Pro Asn Ile Ser Arg Asp Val Val Lys Gln
65                  70                  75                  80

Leu Leu Pro Lys Ala Pro Pro Leu Gln Gln Leu Leu Asp Gln Tyr Asp
                85                  90                  95

Val Leu Gly Asp Asp Ser Lys Asp Gly Ala Val Glu Glu Asp Asp Glu
            100                 105                 110

His Ala Thr Thr Glu Thr Ile Met Thr Met Ala Thr Glu Pro Asp Pro
        115                 120                 125

Ile Val Gln Val Asp Arg Lys Pro Lys Cys Cys Phe Phe Ser Phe Ser
    130                 135                 140

Pro Lys Ile Gln Ala Asn Arg Ile Val Arg Ala Gln Leu Trp Val His
145                 150                 155                 160

Leu Arg Pro Ala Glu Glu Ala Thr Thr Val Phe Leu Gln Ile Ser Arg
                165                 170                 175

Leu Met Pro Val Lys Asp Gly Gly Arg His Arg Ile Arg Ser Leu Lys
            180                 185                 190

Ile Asp Val Asn Ala Gly Val Thr Ser Trp Gln Ser Ile Asp Val Lys
        195                 200                 205

Gln Val Leu Thr Val Trp Leu Lys Gln Pro Glu Thr Asn Arg Gly Ile
    210                 215                 220

Glu Ile Asn Ala Tyr Asp Ala Lys Gly Asn Asp Leu Ala Val Thr Ser
225                 230                 235                 240

Thr Glu Thr Gly Glu Asp Gly Leu Leu Pro Phe Met Glu Val Lys Ile
                245                 250                 255

Ser Glu Gly Pro Lys Arg Ile Arg Arg Asp Ser Gly Leu Asp Cys Asp
            260                 265                 270

Glu Asn Ser Ser Glu Ser Arg Cys Cys Arg Tyr Pro Leu Thr Val Asp
```

```
                    275                 280                 285
Phe Glu Asp Phe Gly Trp Asp Trp Ile Ile Ala Pro Lys Arg Tyr Lys
    290                 295                 300

Ala Asn Tyr Cys Ser Gly Glu Cys Asp Tyr Met Tyr Leu Gln Lys Tyr
305                 310                 315                 320

Pro His Thr His Leu Val Asn Lys Ala Ser Pro Arg Gly Thr Ala Gly
                325                 330                 335

Pro Cys Cys Thr Pro Thr Lys Met Ser Pro Ile Asn Met Leu Tyr Phe
            340                 345                 350

Asn Gly Lys Glu Gln Ile Ile Tyr Gly Lys Ile Pro Ser Met Val Val
        355                 360                 365

Asp Arg Cys Gly Cys Ser
    370

<210> SEQ ID NO 9
<211> LENGTH: 50
<212> TYPE: PRT
<213> ORGANISM: Homo sapiens

<400> SEQUENCE: 9

Lys Asp Val Ile Arg Gln Leu Leu Pro Lys Ala Pro Pro Leu Arg Glu
1               5                   10                  15

Leu Ile Asp Gln Tyr Asp Val Gln Arg Asp Asp Ser Ser Asp Gly Ser
            20                  25                  30

Leu Glu Asp Asp Asp Tyr His Ala Thr Thr Glu Thr Ile Ile Thr Met
        35                  40                  45

Pro Thr
    50

<210> SEQ ID NO 10
<211> LENGTH: 50
<212> TYPE: PRT
<213> ORGANISM: Artificial sequence
<220> FEATURE:
<223> OTHER INFORMATION: Mutant peptide portion of human myostatin

<400> SEQUENCE: 10

Lys Asp Val Ile Arg Gln Leu Leu Pro Lys Ala Pro Pro Leu Arg Glu
1               5                   10                  15

Leu Ile Asp Gln Tyr Asp Val Gln Gln Asp Asp Ser Ser Asp Gly Ser
            20                  25                  30

Leu Glu Asp Asp Asp Tyr His Ala Thr Thr Glu Thr Ile Ile Thr Met
        35                  40                  45

Pro Thr
    50

<210> SEQ ID NO 11
<211> LENGTH: 50
<212> TYPE: PRT
<213> ORGANISM: Artificial sequence
<220> FEATURE:
<223> OTHER INFORMATION: Mutant peptide portion of human myostatin

<400> SEQUENCE: 11

Lys Asp Val Ile Arg Gln Leu Leu Pro Lys Ala Pro Pro Leu Arg Glu
1               5                   10                  15

Leu Ile Asp Gln Tyr Asp Val Gln Arg Ala Asp Ser Ser Asp Gly Ser
            20                  25                  30
```

Leu Glu Asp Asp Asp Tyr His Ala Thr Thr Glu Thr Ile Ile Thr Met
            35                  40                  45

Pro Thr
    50

<210> SEQ ID NO 12
<211> LENGTH: 40
<212> TYPE: PRT
<213> ORGANISM: Homo sapiens

<400> SEQUENCE: 12

Gln Leu Leu Pro Lys Ala Pro Pro Leu Arg Glu Leu Ile Asp Gln Tyr
1               5                   10                  15

Asp Val Gln Arg Asp Asp Ser Ser Asp Gly Ser Leu Glu Asp Asp
            20                  25                  30

Tyr His Ala Thr Thr Glu Thr Ile
        35                  40

<210> SEQ ID NO 13
<211> LENGTH: 40
<212> TYPE: PRT
<213> ORGANISM: Artificial sequence
<220> FEATURE:
<223> OTHER INFORMATION: Mutant peptide portion of human myostatin

<400> SEQUENCE: 13

Gln Leu Leu Pro Lys Ala Pro Pro Leu Arg Glu Leu Ile Asp Gln Tyr
1               5                   10                  15

Asp Val Gln

```
<212> TYPE: PRT
<213> ORGANISM: Artificial sequence
<220> FEATURE:
<223> OTHER INFORMATION: Mutant peptide portion of human myostatin

<400> SEQUENCE: 16

Ala Pro Pro Leu Arg Glu Leu Ile Asp Gln Tyr Asp Val Gln Gln Asp
1               5                   10                  15

Asp Ser Ser Asp Gly Ser Leu Glu Asp Asp Asp Tyr His Ala
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Mutant peptide portion of human myostatin

<400> SEQUENCE: 17

Ala Pro Pro Leu Arg Glu Leu Ile Asp Gln Tyr Asp Val Gln Arg Ala
1               5                   10                  15

Asp Ser Ser Asp Gly Ser Leu Glu Asp Asp Asp Tyr His Ala
            20                  25                  30

<210> SEQ ID NO 18
<211> LENGTH: 20
<212> TYPE: PRT
<213> ORGANISM: Homo sapiens

<400> SEQUENCE: 18

Glu Leu Ile Asp Gln Tyr Asp Val Gln Arg Asp Asp Ser Ser Asp Gly
1               5                   10                  15

Ser Leu Glu Asp
            20

<210> SEQ ID NO 19
<211> LENGTH: 20
<212> TYPE: PRT
<213> ORGANISM: Artificial sequence
<220> FEATURE:
<223> OTHER INFORMATION: Mutant peptide portion of human myostatin

<400> SEQUENCE: 19

Glu Leu Ile Asp Gln Tyr Asp Val Gln Gln Asp Asp Ser Ser Asp Gly
1               5                   10                  15

Ser Leu Glu Asp
            20

<210> SEQ ID NO 20
<211> LENGTH: 20
<212> TYPE: PRT
<213> ORGANISM: Artificial sequence
<220> FEATURE:
<223> OTHER INFORMATION: Mutant peptide portion of human myostatin

<400> SEQUENCE: 20

Glu Leu Ile Asp Gln Tyr Asp Val Gln Arg Ala Asp Ser Ser Asp Gly
1               5                   10                  15

Ser Leu Glu Asp
            20

<210> SEQ ID NO 21
<211> LENGTH: 10
<212> TYPE: PRT
```

```
-continued

<213> ORGANISM: Homo sapiens

<400> SEQUENCE: 21

Tyr Asp Val Gln Arg Asp Asp Ser Ser Asp
1               5                   10

<210> SEQ ID NO 22
<211> LENGTH: 10
<212> TYPE: PRT
<213> ORGANISM: Artificial sequence
<220> FEATURE:
<223> OTHER INFORMATION: Mutant peptide portion of human myostatin

<400> SEQUENCE: 22

Tyr Asp Val Gln Gln Asp Asp Ser Ser Asp
1               5                   10

<210> SEQ ID NO 23
<211> LENGTH: 10
<212> TYPE: PRT
<213> ORGANISM: Artificial sequence
<220> FEATURE:
<223> OTHER INFORMATION: Mutant peptide portion of human myostatin

<400> SEQUENCE: 23

Tyr Asp Val Gln Arg Ala Asp Ser Ser Asp
1               5                   10
```

METALLOPROTEASE ACTIVATION OF MYOSTATIN, AND METHODS OF MODULATING MYOSTATIN ACTIVITY

This application claims the benefit of priority under 35 U.S.C. § 119(e) of U.S. Ser. No. 60/486,863, filed Jul. 10, 2003; U.S. Ser. No. 60/439,164, filed Jan. 9, 2003; and U.S. Ser. No. 60/411,133, filed Sep. 16, 2002; the entire content of each which is incorporated herein by reference.

This invention was made in part with government support under Grant Nos. HD35887, AR47746, and GM63471 awarded by the National Institutes of Health. The United States government has certain rights in this invention.

BACKGROUND OF THE INVENTION

1. Field of the Invention

The invention relates generally to metalloprotease regulation of myostatin activity, and more specifically to methods of using agonists or antagonists of the BMP-1/TLD family of metalloproteases to modulate myostatin activity including, for example, to regulate muscle development in an organism, to methods of identifying agonists and antagonists of such metalloproteases, and to agonists and antagonists so identified.

2. Background Information

Myostatin is a transforming growth factor-$\beta$ (TGF-$\beta$) family member that is essential for proper regulation of skeletal muscle growth. Myostatin is a secreted protein that is expressed specifically by cells of the skeletal muscle lineage during embryonic development and in adult animals; low levels of myostatin mRNA also are present in fat cells in adults animals. During early embryogenesis, myostatin mRNA is detectable in the myotome compartment of developing somites. At later embryonic stages and in postnatal life, myostatin is expressed widely in all skeletal muscles that have been examined.

The function of myostatin was elucidated by gene targeting studies in mice. Mice lacking myostatin demonstrated a dramatic and widespread increase in skeletal muscle mass due to muscle fiber hyperplasia and hypertrophy, indicating that myostatin is a negative regulator of muscle growth. The myostatin gene is highly conserved across evolution, with the predicted mature myostatin protein sequence being identical among mice, rats, humans, chickens, turkeys, and pigs, and highly homologous even with respect to aquatic organisms. The function of myostatin also is conserved, with mutations in the myostatin gene correlating to the double muscling phenotype in cattle.

The role of myostatin in regulating muscle growth and development indicates that methods and compositions that regulate myostatin activity can have a broad variety of applications, including, for example, for treating human diseases and for improving livestock production. With respect to human therapeutic applications, inhibitors of myostatin expression or function can provide a clinical benefit in the treatment of muscle wasting disorders such as muscular dystrophy, cachexia, and sarcopenia. In addition, myostatin deficient animals have a significant reduction in fat accumulation, and the loss of myostatin is protective against the development of obesity and type II diabetes in genetic models in mice. As such, modulation of myostatin activity also can be useful in the treatment of metabolic disorders such as obesity and type II diabetes. Further in this respect, inhibitors of myostatin expression or function not only can be useful for increasing the efficiency of livestock production, but also can result in the production of meat with a lower fat content.

Various strategies for manipulating the biological activities of myostatin have been described. Myostatin is synthesized as a precursor protein that undergoes proteolytic processing to generate an N-terminal fragment termed the "pro peptide" and a C-terminal fragment, a disulfide-linked dimer of which is the biologically active species. Currently described strategies for inhibiting myostatin activity have utilized molecules that can bind the myostatin C-terminal dimer and inhibit its activity. For example, myostatin binds two activin type II receptors, Act RIIA and Act RIIB, in vitro, and expression of a truncated dominant negative form of Act RIIB in transgenic mice resulted in the mice having increases in muscle mass comparable to that of transgenic myostatin knock out mice.

The myostatin pro peptide also has been used to inhibit myostatin activity. Following proteolytic processing, the myostatin pro peptide remains non-covalently associated with the C-terminal dimer and maintains the dimer in a latent, inactive state. The pro peptide has been shown to block the activity of the purified myostatin C-terminal dimer in various in vitro assays, and overexpression of the pro peptide in transgenic mice resulted in a phenotype characteristic of the myostatin null mutation. Follistatin is another protein that acts as a myostatin inhibitor. Follistatin can bind and inhibit the activity of a variety of TGF-$\beta$ family members, including myostatin, and transgenic mice overexpressing follistatin in muscle have dramatic increases in muscle growth, consistent with inhibition of myostatin activity.

The above described inhibitors of myostatin each specifically interact with mature myostatin to inhibit its activity. While inhibiting the activity of a protein such as myostatin using an agent that directly interacts with the protein provides great specificity, such a method can require that all or most of the proteins be bound by the agent for the inhibitory effect to be manifest. An alternative way to inhibit the activity of a protein, particularly a protein that, itself must be activated by a second protein such as an enzyme in order for the first protein to be functional, is to target the second protein. Such a method can be advantageous because activating proteins such as enzymes generally are present at much lower levels than their substrates. As such, there is a greater likelihood that all or most of an activating protein such as an enzyme can be inhibited.

With respect to myostatin, at least two proteases are known to be involved in processing promyostatin, the primary gene product, into a signal peptide, a pro peptide and a C-terminal fragment, the latter of which forms homodimers that have biological myostatin activity. Unfortunately, these proteases also can act on a variety of other proteins and, therefore, agents that target and inhibit these proteases, for example, signal peptidase, likely would have diverse and deleterious effects if administered to a living organism. Thus, a need exists to identify biological molecules that are more specifically involved in regulating myostatin activation and activity. The present invention satisfies this need and provides additional advantages.

SUMMARY OF THE INVENTION

The present invention is based on the identification of proteases that cleave myostatin pro peptide, including when the myostatin pro peptide is present in a complex with a myostatin C-terminal dimer. As such, the proteases can convert a latent inactive myostatin complex, which comprises a myostatin pro peptide associated with a C-terminal myostatin polypeptide, to active myostatin, which is a negative regulator of muscle growth and development. Such proteases, which are exemplified by the metalloprotease bone morphogenic protein-1/tolloid (BMP-1/TLD) family of proteins, provide targets for drugs that can increase or decrease the protease activity and, therefore, increase or decrease myostatin activity. Accordingly, the present invention provides agents that modulate metalloprotease mediated myostatin pro peptide cleavage and activation of myostatin, as well as methods of using such agents, for example, to modulate myostatin activity in an organism. Methods of identifying such agents also are provided.

The present invention relates to a method of modulating myostatin activation. Such a method can be performed, for example, by contacting a latent myostatin complex, which includes a myostatin pro peptide and a myostatin C-terminal fragment, particularly a C-terminal fragment dimer, with a metalloprotease that can cleave the myostatin pro peptide, and with an agent that can increase or decrease proteolytic cleavage of the pro peptide by the metalloprotease, thereby modulating myostatin activation. The metalloprotease can be any metalloprotease that can cleave the myostatin pro peptide, particularly when the pro peptide comprises a latent myostatin complex, including, for example, a BMP-1/TLD family member such as BMP-1, TLD, tolloid-like protein-1 (TLL-1), or tolloid-like protein-2 (TLL-2), particularly mammalian BMP-1/TLD family members such as mammalian (m) TLD (mTLD), mTLL-1, and mTLL-2.

A method of the invention can be used to increase the level of myostatin activation (i.e., above a baseline level of myostatin activation in the absence of an agent), for example, by contacting a latent myostatin complex and metalloprotease with an agent that increases proteolytic cleavage of the pro peptide by the metalloprotease; or can be used to decrease the level of myostatin activation (below a baseline level), for example, by contacting a latent myostatin complex and metalloprotease with an agent that decreases proteolytic cleavage of the pro peptide by the metalloprotease. The method can be performed in vitro, using, for example, cells or a tissue in culture, a cell extract, or substantially purified reagents, including substantially purified metalloprotease and/or latent myostatin complex; or can be performed in vivo, for example, in a cell or tissue, either of which can be in situ in an organism or isolated from an organism (e.g., a cell ex vivo, which can be in culture). Thus, the method can be performed by contacting a sample comprising a latent myostatin complex and metalloprotease (e.g., a tissue sample and/or a biological fluid) with an agent in vitro, or the contacting can be performed in vivo, for example, by administering the agent to a subject.

Free myostatin pro peptide, latent myostatin complex, and a metalloprotease that can cleave a myostatin pro peptide can be present intracellularly or extracellularly. However, the pro peptide or latent myostatin complex generally is not present in the same cells or cell type as the metalloprotease and, therefore, cleavage of myostatin pro peptide by the metalloprotease generally occurs extracellularly upon contact of the metalloprotease with the pro peptide. As such, contacting of an agent with the pro peptide, complex, and/or metalloprotease will depend in part on how the agent acts to modulate the cleavage. For example, where the agent can bind to and alter the conformation of the metalloprotease so as to inhibit its cleavage activity with respect to a myostatin pro peptide, cells that produce the metalloprotease can be contacted with the agent such that the secreted metalloprotease lacks such activity, or the agent can be administered to a medium into which the metalloprotease is secreted (e.g., into the bloodstream of a living organism) such that, upon contact with the agent in the medium, the cleavage of the pro peptide by the metalloprotease is reduced or inhibited. In comparison, where the agent acts, for example, to destabilize an interaction of the metalloprotease and the pro peptide, or where the agent acts as a competitive or non-competitive inhibitor of the metalloprotease with respect to the pro peptide, the agent generally is contacted with the medium in which the metalloprotease and pro peptide are likely to interact (e.g., the blood).

In one embodiment, the agent decreases proteolytic activity of a metalloprotease that cleaves myostatin pro peptide from a latent myostatin complex, thereby reducing or inhibiting myostatin activation below a level of myostatin activation that occurs or would occur in the absence of the agent. Where such an agent is administered to a subject, the agent can result in increased muscle mass or decreased fat content or both in the subject. The subject can be any subject in which myostatin is expressed, particularly a vertebrate organism, for example, animals that are raised as a food source, such as a mammalian species (e.g., an ovine, porcine species, or bovine species), avian species (e.g, chickens or a turkeys), or a piscine species (e.g., salmon, trout, or cod). The subject also can be a human subject, for example, a subject suffering from a muscular disorder (e.g., a dystonia or dystrophy), a subject suffering from wasting disorder (e.g., cachexia), or a subject suffering from clinical obesity or other metabolic disorder such as type II diabetes. In another embodiment, the agent increases proteolytic activity of a metalloprotease that cleaves myostatin pro peptide from a latent myostatin complex, thereby increasing myostatin activation above a level, if any, of myostatin activation that occurs or would occur in the absence of the agent. Where such an agent is administered to a subject, the agent can result in decreased muscle mass or increased fat content or both in the subject.

The present invention also relates to a method of increasing muscle mass in a subject. Such a method can be performed, for example, by administering to the subject an agent that reduces or inhibits proteolytic cleavage of a myostatin pro peptide by a protease that cleaves myostatin pro peptide, thereby preventing activation of latent myostatin in the cell and increasing muscle mass in the subject. The metalloprotease can be any metalloprotease, particularly a BMP-1/TLD family member such as BMP-1, TLD, TLL-1, or TLL-2, including mTLD, mTLL-1 and mTLL-2. The subject in which muscle mass is to be increased generally is vertebrate, for example, a domesticated or farm animal, including a mammal such as an ovine species, a porcine species, or a bovine species; an avian species such as a chicken or a turkey; or a piscine species; or can be a human subject.

The present invention further relates to a method for ameliorating a metabolic disorder in a subject. Such a method can be performed, for example, by administering to the subject an agent that reduces or inhibits the proteolytic cleavage of a myostatin pro peptide by a protease that cleaves myostatin pro peptide, thereby preventing activation of latent myostatin in the cell and ameliorating the metabolic disorder. The metabolic disorder can be any such disorder associated with increased or undesirable myostatin activation or activity, including, for example, a muscle wasting disorder such as is associated with muscular dystrophy, cachexia (e.g., associated with a cancer or acquired immunodeficiency disease), or sarcopenia; or a metabolic disorder such as clinical obesity or type 2 diabetes. The subject in which the metabolic disorder is ameliorated can be any subject, and generally is a vertebrate subject, for example, a domesticated animal such as a cat or dog, or an animal raised as a source of food (e.g., cattle, sheep, pigs, or fish); or can be a human subject. Amelioration of the disorder can be identified using any assay generally used to monitor the particular metabolic disorder, for example, a glucose tolerance test for diabetes, or a serum leptin assay for body fat analysis.

The present invention also relates to a method of identifying an agent that modulates metalloprotease mediated myostatin pro peptide cleavage and activation of latent myostatin. Such a screening method can be performed, for example, by contacting a myostatin pro peptide, a metalloprotease that can cleave the myostatin pro peptide, and a test agent, under conditions sufficient for cleavage of the pro peptide by the metalloprotease; and detecting a change in the amount of cleavage of the pro peptide in the absence of the test agent as compared to the presence of the test agent, thereby identifying the test agent as an agent that modulates metalloprotease mediated activation of the latent myostatin. The myostatin pro peptide can be in an isolated form, or can be a component of a latent myostatin complex that further contains a myostatin C-terminal fragment or a myostatin C-terminal dimer.

Where a test agent is identified as having metalloprotease mediated myostatin modulating activity, a screening assay of the invention can further include a step of determining an amount by which the agent increases or decreases myostatin pro peptide cleavage or myostatin activation. For example, where an agent is identified that increases the proteolytic activity of the metalloprotease above a basal level in a cell, a method of the invention can further include determining an amount by which the agent increases myostatin activation above the basal level. As such, a method of the invention provides a means to obtain agents or panels of agents that variously modulate myostatin activation by a metalloprotease. Such a method further provides a means to determine amounts of a particular agent useful for providing a desired level of myostatin activity.

A difference in the amount of cleavage of the pro peptide due to contact with a test agent can be detected, for example, by detecting the pro peptide or a cleavage product of the pro peptide using a method such as electrophoresis, chromatography, or mass spectrometry, which can detect a myostatin pro peptide or cleavage product thereof based on its size, charge, or both; an immunological based assay such as an immunoblot analysis, an enzyme-linked immunosorption assay (ELISA), or the like, which utilizes an antibody specific for the intact pro peptide or the cleaved pro peptide, but not an antibody that binds both the intact and the cleaved pro peptide; or a fluorescence based assay, including, for example, a fluorescence resonance energy transfer (FRET) assay, wherein fluorescence of the intact pro peptide is quenched, and the quenching is relieved upon cleavage of the pro peptide. Depending on the relative amount of intact myostatin pro peptide, pro peptide cleavage product, or a combination thereof that is detected, a test agent can be identified as an agent that increases or decreases metalloprotease mediated myostatin pro peptide cleavage and activation of the latent myostatin.

A difference in the amount of cleavage of the pro peptide also can be detected by detecting a change in binding of myostatin to a myostatin receptor in vitro or expressed on a cell surface, or by detecting a change in a myostatin mediated signal transduction in a cell expressing a myostatin receptor. Where the assay is a cell based assay, the cell can be one that expresses an endogenous myostatin receptor, for example, L6 myocytes, or can be a cell expressing a transgene encoding the myostatin receptor, for example, a cell transfected with a polynucleotide encoding an activin receptor such as an activin type II receptor. Myostatin mediated signal transduction can be detected at any level in the signal transduction pathway, including from binding of myostatin to a cell surface receptor to expression of a gene that is regulated due to myostatin binding to a myostatin receptor, wherein, in a screening assay of the invention, the signal transduction is dependent on metalloprotease mediated cleavage of a myostatin pro peptide and activation of a latent myostatin complex. As such, myostatin mediated signal transduction can be detected by detecting myostatin binding to a myostatin receptor using a receptor binding assay, or by detecting expression of a myostatin regulated gene, including, for example, a reporter gene, which can comprise, for example, a TGF-β regulatory element operatively linked to a polynucleotide encoding a detectable polypeptide. Accordingly, the present invention provides agents that modulate metalloprotease mediated myostatin pro peptide cleavage and myostatin activation, wherein the agents are identified using a screening assay of the invention. The present methods also are useful for confirming that an agent modulates metalloprotease mediated myostatin pro peptide cleavage and myostatin activation, including, if desired, the specific activity of the agent.

The present invention also relates to an agent that modulates metalloprotease mediated activation of latent myostatin. The agent can be an agonist or an antagonist of metalloprotease mediated activation of latent myostatin, and can reduce or inhibit metalloprotease mediated activation of latent myostatin, or can increase metalloprotease mediated activation of latent myostatin. An agent that modulates metalloprotease mediated activation of latent myostatin can be any type of molecule, including, for example, a peptide agent, a polynucleotide agent, an antibody agent, or a small organic molecule agent.

An agent that modulates metalloprotease mediated activation of latent myostatin is exemplified herein by a peptide agent. A peptide agent can include, for example, a peptide portion of a myostatin polypeptide, or a derivative of such a peptide portion of myostatin. In one embodiment, a derivative of a peptide portion of myostatin is a peptide that corresponds to a myostatin pro peptide. In one aspect of this embodiment, the derivative is a pro peptide having a mutation of the metalloprotease cleavage site, for example, a substitution, deletion, or insertion of an amino acid at or in sufficient proximity to the cleavage site such that the metalloprotease has increased or decreased cleavage activity with respect to the peptide agent. In another aspect of this embodiment, the derivative of a peptide portion of myostatin is a peptide agent that reduces or inhibits metalloprotease mediated activation of latent myostatin. The agent that modulates metalloprotease mediated activation of latent myostatin can be operatively linked to a second molecule, which facilitates the action or activity of the agent, or increases or decreases the stability of the agent in a particular environment. For example, a peptide agent can be stabilized by operatively linking the peptide agent to a polypeptide such as an Fc domain of an antibody molecule, thereby increasing the half-life of the peptide agent in vivo.

BRIEF DESCRIPTION OF THE DRAWINGS

FIGS. 3A and 3B show detection of a pro peptide degradation product in CHO cell conditioned media. Conditioned media prepared from CHO cells expressing the pro peptide (FIG. 3A) or wild type and mutant forms of pro peptide/Fc fusion proteins (FIG. 3B) were analyzed by SDS-PAGE followed by western blot analysis using antibodies directed against either the myostatin pro peptide (FIG. 3A) or IgG (FIG. 3B). Note that mutation of D76 to A resulted in loss of the degradation product.

FIG. 3C shows purification of wild type and mutant pro peptide/C-terminal dimer complexes. Protein complexes were analyzed by SDS-PAGE in the presence or absence of β-mercaptoethanol followed by western blot analysis, as indicated. Note that like the wild type pro peptide, the D76A mutant pro peptide purified in a complex with the C-terminal dimer. The pro peptide degradation product did not co-purify with and was thus not part of the complex. Bands denoted by the asterisk indicate misfolded myostatin species, which were evident under non-reducing conditions.

FIGS. 3D and 3E show cleavage of the pro peptide by BMP-1/TLD proteinases. Wild type and mutant complexes were incubated with purified proteinases and analyzed by SDS-PAGE followed by western blotting using antibodies directed against the pro peptide. Incubations were carried out with 1 μg latent complex and 250 ng proteinase for 16 hours at 37° C., except that in FIG. 3D, the samples were incubated with an additional 250 ng BMP-1 for 4 more hours. In FIG. 3E, lanes labeled "no enzyme" indicate samples incubated for 16 hours at 37° C. in the absence of enzyme. Note that all enzymes were capable of generating the cleavage product and that the D76A mutant protein was completely resistant to cleavage.

In FIGS. 4B to 4D, black bars represent wild type, and gray bars represent D76A mutant complexes. Note that although heat treatment activated both the wild type and mutant complexes (FIG. 4B), each proteinase was capable of activating only the wild type complex (FIGS. 4C and 4D). *$p<0.05$, **$p<0.01$.

FIG. 4A shows activation of pGL3-(CAGA)$_{12}$-luciferase reporter gene activity by purified myostatin C-terminal dimer.

FIG. 4B shows activation of the myostatin pro peptide/C-terminal dimer latent complex by heat treatment. Control (no myostatin (MSTN)) is indicated.

FIGS. 4C and 4D show activation of the myostatin pro peptide/C-terminal dimer latent complex by BMP-1/TLD proteinases. The samples used for the reporter assays in FIGS. 4C and 4D are the same samples shown in FIGS. 3D and 3E, respectively.

DETAILED DESCRIPTION OF THE INVENTION

Figure 1:
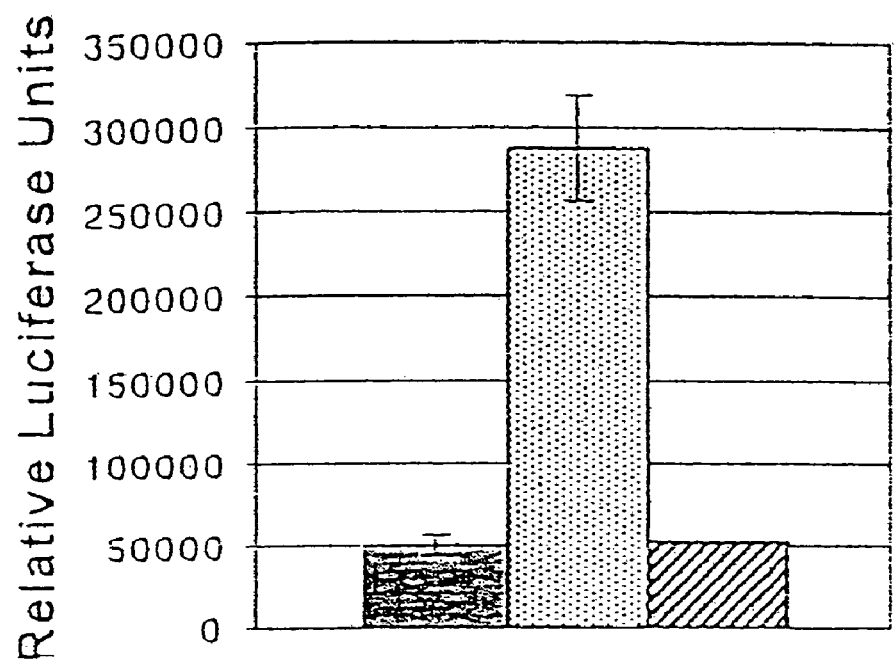
FIG. 1 demonstrates that incubation of the myostatin complex (MSTN; C-terminal myostatin dimer and pro peptide) with mTLL-1 resulted in a dramatic increase in expression of a luciferase reporter gene (stippled bar; see Example 2), the expression of which is regulated in transfected rhabdomyosarcoma cells upon contact of the cells with active myostatin. Only background expression was observed in cells contacted with myostatin complex, alone (solid bar), or with mTLL-1, alone (hatched bar).

The present invention is based on the identification of proteases that cleave myostatin pro peptide, including when the pro peptide is present in a complex with a myostatin C-terminal dimer, thereby converting latent inactive myostatin complex to active myostatin. Proteases having such myostatin pro peptide cleaving activity are exemplified by the metalloprotease bone morphogenic protein-1/tolloid (BMP-1/TLD) family of proteins. As such, the proteases provide targets and reagents for identifying drugs that can increase or decrease the protease activity, or can increase or decrease myostatin pro peptide cleavage mediated by the proteases, and, therefore, increase or decrease myostatin activity.

Myostatin (growth differentiation factor-8; GDF-8) is expressed as a pre-proprotein, promyostatin, which includes a signal peptide (amino acid residues about 1 to 20), the myostatin pro peptide domain (amino acid residues about 20 to 262 or 263) and the myostatin C-terminal domain (amino acid residues about 267 or 268 to 375). Promyostatin polypeptides and encoding polynucleotides are highly conserved evolutionarily (see McPherron and Lee, *Proc. Natl. Acad. Sci., USA* 94:12457, 1997; GenBank Acc. Nos. AF019619, AF019620, AF019621, AF019622, AF019623, AF019624, AF019625, AF019626, and AF019627; U.S. Pat. No. 5,994,618, each of which is incorporated herein by reference). Promyostatin polynucleotides and encoded polypeptides are exemplified herein by human promyostatin (SEQ ID NOS:1 and 2; pro peptide is amino acid residues about 20 to 263), bovine promyostatin (SEQ ID NOS:3 and 4; pro peptide is amino acid residues about 20 to 262), chicken promyostatin (SEQ ID NOS:5 and 6; pro peptide is amino acid residues about 20 to 262), and zebrafish promyostatin (SEQ ID NOS:7 and 8; pro peptide is amino acid residues about 20 to 262).

Myostatin is activated by two proteolytic cleavage events—a first removing the signal sequence (approximately the first 20 N-terminal amino acid residues of promyostatin; see, for example, SEQ ID NO:2), and a second at a tetrabasic processing site (at about amino acid residues 263 to 266 of promyostatin)—resulting in the generation of a 26 kDa N-terminal pro peptide (approximately amino acid residues 20 to 262 or 263) and a 12.5 kDa C-terminal peptide (approximately amino acid residue 266 or 267 to the C-terminus); a dimer of the C-terminal peptide is biologically active. Upon secretion from cells, the myostatin C-terminal dimer is maintained in a latent, inactive state due to its remaining bound to the myostatin pro peptide (Lee and McPherron, *Proc. Natl. Acad. Sci., USA* 98:9306-9311, 2001, which is incorporated herein by reference). The latent myostatin complex that circulates in the blood of adult mice can be activated in vitro by treatment with acid (Zimmers et al., *Science* 296:1486-1488, 2002, which is incorporated herein by reference).

Mice in which the myostatin gene has been knocked out show increased muscle mass, and further exhibit a significant reduction in fat accumulation with increasing age as compared to wild type littermates (McPherron and Lee, *J. Clin. Invest.* 109:595-601, 2002, which is incorporated herein by reference). Conversely, over-expression of myostatin in vivo produces the signs and symptoms characteristic of the muscle wasting syndrome, cachexia (Zimmers et al., supra, 2002). The muscle wasting observed in mice having increased levels of circulating myostatin can be partially reversed by introducing myostatin binding agents such as the myostatin pro peptide and follistatin to the mice (Zimmers et al., supra, 2002). These results confirmed that the observed muscle wasting was due to increased myostatin, and indicate that methods for decreasing the level of active myostatin or otherwise reducing or inhibiting myostatin activity can be useful for ameliorating muscle wasting. In view of the highly conserved nature of myostatin among species as diverse as fish and humans, these results indicate that myostatin also can be involved in the cachexia associated with various disorders in humans, including, for example, cancer, acquired immunodeficiency syndrome (AIDS), and sepsis, as well as in neuromuscular disorders such as muscular dystrophy (see Gonzalez-Kadavid et al., *Proc. Natl. Acad. Med., USA* 95:14938-14943, 1998, which is incorporated herein by reference).

Proper skeletal muscle function also is involved in maintaining normal glucose metabolism, and skeletal muscle resistance to insulin stimulated glucose uptake is the earliest manifestation of non-insulin dependent (type 2) diabetes (see McPherron and Lee, supra, 2002). In two mouse models of obesity and diabetes, loss of myostatin prevented an increase in adipose tissue mass with age and attenuated the obese and diabetic phenotype in the mouse models (McPherron and Lee, supra, 2002). As such, methods that modulate myostatin activity also can be useful for reducing body fat in an individual, and for treating disorders associated with abnormal muscle function or obesity, for example, type 2 diabetes.

As disclosed herein, the myostatin pro peptide, either in a free form or when part of a complex with the myostatin C-terminal dimer, can be cleaved by members of the BMP-1/TLD family of metalloproteases, and such cleavage releases the myostatin C-terminal dimer from the inhibitory effects of the pro peptide, thus generating active myostatin. As such, the BMP-1/TLD proteases provide a target for drugs that can modulate myostatin activity and, therefore, increase or decrease muscle mass or reduce or prevent obesity in an organism. Accordingly, the invention provides methods of identifying agents that modulate metalloprotease mediated myostatin pro peptide cleavage, and that modulate metalloprotease mediated activation of latent myostatin.

A screening method of the invention can be performed, for example, by contacting a myostatin pro peptide, a metalloprotease that can cleave the myostatin pro peptide, and a test agent, under conditions sufficient for cleavage of the pro peptide by the metalloprotease; and detecting a change in the amount of cleavage of the pro peptide in the absence of the test agent as compared to the presence of the test agent, thereby identifying the test agent as an agent that modulates metalloprotease mediated myostatin pro peptide cleavage. The myostatin pro peptide can be in an isolated form, or can be a component of a latent myostatin complex that further contains a myostatin C-terminal fragment or a myostatin C-terminal dimer.

A metalloprotease examined according to a screening assay of the invention can be any protease that cleaves a myostatin pro peptide, particularly a metalloprotease that cleaves the pro peptide when it is in a latent myostatin complex with a C-terminal myostatin fragment or dimer thereof, such that active myostatin is generated from the latent myostatin complex. Such metalloproteases are exemplified by the BMP-1/TLD family of metalloproteases, which includes four mammalian proteins, BMP-1 (Wozney et al., *Science* 242:1528-1534, 1988), mammalian Tolloid (mTLD; Takahara et al., *J. Biol. Chem.* 269:32572-32578, 1994), mammalian Tolloid-like-1 (mTLL-1; Takahara et al., *Genomics* 34:157-165, 1996), and mammalian Tolloid-like-2 (mTLL-2; Scott et al., *Devel. Biol.* 213:283-300, 1999). The BMP-1/TLD family of metalloproteases, in turn, are members of a larger family of proteins, the astacin family, which includes proteases that are expressed in various vertebrate and invertebrate organisms, including, for example, *Xenopus* (Xolloid; UVS.2), fish (choriolysin H and L; zebrafish Tolloid), sea urchin (BP-10 and SpAN), and hydra (HMP-1; see, for example, Li et al., *Proc. Natl. Acad Sci., USA* 93:5127-5130, 1996, which is incorporated herein by reference). As such, the screening assays of the invention can be practiced using any of various metalloproteases and, therefore, allow an identification of agents that can be useful, for example, for modulating myostatin activation in a variety of different organisms.

BMP-1 and mTLD are encoded by alternatively spliced mRNAs from a single gene (Takahara et al., supra, 1994), whereas mTLL-1 and mTLL-2 are encoded by distinct genes. The BMP-1/TLD family of proteases is known to have a role in regulating the activity of at least three classes of substrates. First, BMP-1, mTLD, and mTLL-1 are capable of processing procollagen precursors into the mature monomers required for assembly into the multimeric fibers that are normally present in the extracellular matrix (Kessler et al., *Science* 271:360-362, 1996; Li et al., supra, 1996). Second, BMP-1, mTLD, mTLL-1 and mTLL-2 each can process pro-lysyl oxidase into the mature, biologically active enzyme (Uzel et al., *J. Biol. Chem.* 276:22537-22543, 2001). Third, BMP-1 and mTLL-1 can cleave chordin (Scott et al., supra, 1999), which normally binds various members of the BMP subgroup of the TGF-β superfamily and maintains them in a latent state (Blader et al., *Science* 278:1937-1940, 1997; Marques et al., *Cell* 91:417-26, 1997; Piccolo et al., *Cell* 91:407-416, 1997). Cleavage of chordin by these metalloproteases releases the BMP from the inhibitory effect of chordin. As such, BMP-1 and TLL-1 are believed have a role in modulating the effects of the BMPs during a variety of morphogenic processes. As disclosed herein, BMP-1/TLD family members, including BMP-1, mTLD, mTLL-1 and mTLL-2 also can cleave the myostatin pro peptide, either in its free form or when bound to the myostatin C-terminal dimer (latent myostatin complex), wherein cleavage of the pro peptide results in activation of the myostatin C-terminal dimer (see Examples 1 and 2).

A test agent that can be examined according to a method of the invention can be any type of molecule, including, for example, a peptide, peptide derivative such as a peptide hydroxamate or a phosphinic peptide, peptoid, polynucleotide, or small organic molecule (see Example 3). Thus, the term "test agent" is used broadly herein to mean any compound that is being examined for agonist or antagonist activity with respect to metalloprotease mediated myostatin pro peptide cleavage or myostatin activation. Although the method generally is used as a screening assay to identify previously unknown molecules (test agents) that can act as agonist or antagonist agents, the method also can be used to confirm that an agent known to have a particular activity in fact has the activity, for example, in standardizing the activity of the agent; and can be used to screen derivatives or other modified forms or mimics of such known agents.

A screening method of the invention conveniently can be adapted to high throughput analysis and, therefore, can be used to screen combinatorial libraries of test agents, which can be a library of random test agents, biased test agents, or variegated test agents (see, for example, U.S. Pat. No. 5,571,698, which is incorporated herein by reference), in order to identify those agents that can modulate metalloprotease mediated cleavage of a myostatin pro peptide and, therefore, myostatin activity. Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a library of peptide derivative compounds such as a hydroxamate compound library, reverse hydroxamate compound library, a carboxylate compound library, thiol compound library, a phosphinic peptide library, or phosphonate compound library (see, for example, Dive et al., *Biochem. Soc. Trans.* 28:455-460, 2000; Ye and Marshall, *Peptides: The Wave of the Future* (Lebl and Houghten, ed.; American Peptide Society, 2001), each of which is incorporated herein by reference); a peptidomimetic library (Blondelle et al., *Trends Anal. Chem.* 14:83-92, 1995, which is incorporated herein by reference); a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995; each of which is incorporated herein by reference); a lipoprotein library (de Kruif et al., *FEBS Lett.* 399:232-236, 1996, which is incorporated herein by reference); a glycoprotein or glycolipid library (Karaoglu et al., *J. Cell Biol.* 130:567-577, 1995, which is incorporated herein by reference); or a chemical library containing, for example, drugs or other pharmaceutical agents (Gordon et al., *J. Med. Chem.* 37:1385-1401, 1994; Ecker and Crooke, *BioTechnology* 13:351-360, 1995; each of which is incorporated herein by reference).

Polynucleotides can be particularly useful as agents that can modulate metalloprotease mediated myostatin pro peptide cleavage or myostatin activation because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference). The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. A polynucleotide can be a naturally occurring nucleic acid molecule, which can be isolated from a cell, or a synthetic molecule, which can be prepared, for example, by methods of chemical synthesis or by enzymatic methods such as by the polymerase chain reaction (PCR).

A polynucleotide agent (or test agent) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994; Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Similarly, peptides, as exemplified herein (see Examples 3 and 4) can be useful as agents for modulating metalloprotease mediated myostatin activation, or as test agents to screen for such activity. Peptide agents (or test peptides) can contain one or more D-amino acids and/or L-amino acids; and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment, and, therefore, can be particularly useful in performing a method of modulating metalloprotease mediated myostatin activation as disclosed herein. As disclosed herein, the stability of a peptide agent (or test agent) also can be improved by generating (or linking) a fusion protein comprising the peptide and a second polypeptide (e.g., an Fc domain of an antibody) that increases the half-life of the peptide agent in vivo (see Example 4; see, also, U.S. patent application Publication No. US 2003/0104406 A1, which is incorporated herein by reference). Peptides also can be modified to have decreased stability in a biological environment, if desired, such that the period of time the peptide is active in the environment is reduced.

Test agents also can be antibodies that are raised against and specifically bind one or more epitopes of a metalloprotease that cleaves a myostatin pro peptide; or against an epitope of the pro peptide, which can be an isolated pro peptide or a pro peptide component of a latent myostatin complex; or a complex of the metalloprotease and pro peptide. As used herein, the term "antibody" is used in its broadest sense to include polyclonal and monoclonal antibodies, as well as antigen binding fragments of such antibodies. The term "binds specifically" or "specific binding activity" or the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, F(ab')$_2$, Fd and Fv fragments of an antibody that retain specific binding activity are included within the definition of an antibody. In addition to specifically binding a particular epitope, an antibody agent modulates the protease cleavage activity of a metalloprotease for a myostatin pro peptide, including increasing or decreasing such activity.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1999); Hilyard et al., *Protein Engineering: A practical approach* (IRL Press 1992); Borrabeck, *Antibody Engineering*, 2d ed. (Oxford University Press 1995); each of which is incorporated herein by reference).

A panel of test agent antibodies conveniently can be obtained by immunizing an animal using a peptide portion of a myostatin pro peptide or of a metalloprotease, particularly a BMP-1/TLD family member. Where such a peptide portion of the pro peptide or metalloprotease is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1999). Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1; each or which is incorporated herein by reference). In addition, monoclonal antibodies can be obtained using methods that are well known and routine in the art (see, for example, Kohler and Milstein, *Nature* 256:495, 1975, which is incorporated herein by reference; see, also, Harlow and Lane, supra, 1999). For example, spleen cells from a mouse immunized with a myostatin receptor, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. A recombinant phage that expresses, for example, a single chain antibody that modulates metalloprotease mediated cleavage of myostatin pro peptide also provides an antibody that can used for preparing standardized kits.

Monoclonal antibodies can be isolated and purified from hybridoma cultures by a variety of well established techniques, including, for example, affinity chromatography with Protein-A SEPHAROSE gel, size exclusion chromatography, and ion exchange chromatography (Coligan et al., supra, 1992, see sections 2.7.1-2.7.12 and sections 2.9.1-2.9.3; see, also, Barnes et al., "Purification of Immunoglobulin G (IgG)," in *Meth. Molec. Biol.* 10:79-104 (Humana Press 1992), which is incorporated herein by reference). Methods of in vitro and in vivo multiplication of monoclonal antibodies are well known in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibody agents identified according to a screening assay of the invention also are provided. Where the therapeutic procedure is for treating a human subject, the antibodies can be derived from a subhuman primate antibody (see, for example, Goldenberg et al., Intl. Publ. WO 91/11465, 1991; and Losman et al., *Intl. J. Cancer* 46:310, 1990, each of which is incorporated herein by reference). A therapeutically useful antibody for human treatment also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are known (see, for example, Orlandi et al., *Proc. Natl. Acad. Sci., USA* 86:3833, 1989, which is hereby incorporated in its entirety by reference). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci., USA* 89:4285, 1992; Sandhu, *Crit. Rev. Biotechnol.* 12:437, 1992; and Singer et al., *J. Immunol.* 150:2844, 1993; each of which is incorporated herein by reference). Alternatively, the antibodies can be derived from human antibody fragments isolated from a combinatorial immunoglobulin library (see, for example, Barbas et al., *METHODS: A Companion to Methods in Immunology* 2:119, 1991; Winter et al., *Ann. Rev. Immunol.* 12:433, 1994; each of which is incorporated herein by reference).

The antibodies also can be derived from human monoclonal antibodies, which, for example, can be obtained from transgenic mice that have been genetically modified to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are well known (see, for example, by Green et al., *Nature Genet.* 7:13, 1994; Lonberg et al., *Nature* 368:856, 1994; and Taylor et al., *Intl. Immunol.* 6:579, 1994; each of which is incorporated herein by reference), and commercial sources of human antibodies are available (Abgenix, Inc.; Fremont Calif.).

Antigen binding fragments of an antibody can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment, F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. Nos. 4,036,945 and 4,331,647, each of which is incorporated by reference, and references contained therein; Nisonhoff et al., *Arch. Biochem. Biophys.* 89:230, 1960; Porter, *Biochem. J.* 73:119, 1959; Edelman et al., *Meth. Enzymol.* 1:422 (Academic Press 1967), each of which is incorporated herein by reference; see, also, Coligan et al., supra, 1992, see sections 2.8.1-2.8.10 and 2.10.1-2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains; this association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde ( Sandhu, supra, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *METHODS: A Companion to Methods in Enzymology* 2:97, 1991; Bird et al., *Science* 242:423-426, 1988; Ladner et al., U.S. Pat. No. 4,946,778; Pack et al., *BioTechnology* 11:1271-1277, 1993; each of which is incorporated herein by reference; see, also Sandhu, supra, 1992. Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *METHODS: A Companion to Methods in Enzymology* 2:106, 1991, which is incorporated herein by reference).

A difference in the amount of cleavage of the pro peptide due to contact with a test agent can be detected, for example, by detecting the pro peptide and/or a cleavage product of the pro peptide using a method such as electrophoresis, chromatography, or mass spectrometry (see, for example, Thies et al., *Growth Factors* 18:251-259, 2001, which is incorporated herein by reference), which can detect a myostatin pro peptide or cleavage product thereof based on its size, charge, or both; an immunological based assay such as an immunoblot analysis, an enzyme-linked immunosorption assay (ELISA), or the like, which utilizes an antibody specific for the intact pro peptide or the cleaved pro peptide, but not both; or a fluorescence based assay, including, for example, a fluorescence resonance energy transfer (FRET) assay, wherein fluorescence of the intact pro peptide is quenched, and the quenching is relieved upon cleavage of the pro peptide. Where an increased amount of a cleavage product of the pro peptide is detected in the presence of (or following contact with) the test agent as compared to an amount of cleavage product in the absence of the test agent, the test agent is identified as an agent that can increase metalloprotease mediated activation of the latent myostatin. Similarly, where a decreased amount of the pro peptide is detected in the presence of (or following contact with) the test agent as compared to an amount of pro peptide in the absence of the test agent, the test agent is identified as an agent that can increase metalloprotease mediated activation of the latent myostatin. Conversely, where a decreased amount of a cleavage product of the pro peptide is detected in the presence of (or following contact with) the test agent as compared to an amount of cleavage product in the absence of the test agent, the test agent is identified as an agent that can decrease metalloprotease mediated activation of the latent myostatin. Where a greater amount of the pro peptide is detected in the presence of (or following contact with) the test agent as compared to an amount of pro peptide in the absence of the test agent, the test agent is identified as an agent that can decrease metalloprotease mediated activation of the latent myostatin. Such activity can be confirmed using a cell based or animal assay by detecting, for example, a change in myostatin mediated signal transduction activity due to the agent.

A difference in the amount of cleavage of the pro peptide also can be detected by detecting a change in binding of myostatin to a myostatin receptor, or by detecting a change in a myostatin mediated signal transduction in a cell expressing a myostatin receptor. Cells useful for performing a screening assay of the invention include, for example, cells from mammals, birds, fish, yeast, or *Drosophila*. Such functional assays can directly indicate that a test agent modulates metalloprotease mediated myostatin activation. A cell useful for such a method can be one that expresses an endogenous myostatin receptor, for example, L6 myocytes, or can be a cell genetically modified, transiently or stably, to express a transgene encoding the myostatin receptor, for example, an activin receptor such as an activin type II receptor (Thies et al., supra, 2001). Myostatin mediated signal transduction can be detected at any level in the signal transduction pathway, including from binding of myostatin to a cell surface receptor to expression of a gene that is regulated by myostatin, which, in a screening assay of the invention, is dependent on metalloprotease mediated cleavage of a myostatin pro peptide and myostatin activation.

Metalloprotease mediated myostatin activation and consequent myostatin mediated signal transduction can be detected by measuring myostatin binding to a myostatin receptor using a receptor binding assay, which can be an in vitro assay or cell based assay. Metalloprotease mediated myostatin activation and consequent myostatin mediated signal transduction also can be detected by measuring expression of a myostatin regulated gene, which can be a reporter gene comprising, for example, a TGF-β regulatory element operatively linked to a polynucleotide encoding a detectable label. Expression of the reporter gene can be detected, for example, by detecting an RNA transcript of the reporter gene sequence, or by detecting a polypeptide encoded by the reporter gene or an activity of the encoded polypeptide. A polypeptide reporter can be, for example, β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase, or xanthine guanine phosphoribosyltransferase, and can be detected, for example, by detecting radioactivity, luminescence, chemiluminescence, fluorescence, enzymatic activity, or specific binding due to the reporter polypeptide, or survival in a selective medium of cells expressing the reporter polypeptide. Methods for introducing a transgene such as a polynucleotide encoding a myostatin receptor or a reporter gene under conditions such that a polypeptide encoded by the transgene can be expressed are disclosed herein or otherwise known in the art.

Generally, a reporter gene includes a coding sequence, which encodes the reporter polynucleotide or polypeptide, operatively linked to one or more transcription and, as appropriate, translation regulatory elements, and can be contained in a vector, particularly an expression vector. If desired, the coding sequence can further encode an operatively linked peptide tag such as a His-6 tag, which can be detected using a divalent cation such as nickel ion, cobalt ion, or the like; a FLAG epitope, which can be detected using an anti-FLAG antibody (see, for example, Hopp et al., *BioTechnology* 6:1204, 1988,; U.S. Pat. No. 5,011,912, each of which is incorporated herein by reference); a c-myc epitope, which can be detected using an antibody specific for the epitope; biotin, which can be detected using streptavidin or avidin; glutathione S-transferase, which can be detected using glutathione; or an Fc domain of an antibody, which can be detected using Protein A or an anti-Fc antibody, either of which, can, but need not, be detectably labeled or attached to a solid support or, in turn, detected using a second antibody. As such, it will be recognized that various means for detecting a particular tagged molecule also can be used to isolate the tagged molecule.

As used herein, the term "operatively linked" means that two or more molecules are positioned with respect to each other such that they act as a single unit and effect a function attributable to one or both molecules or a combination thereof. For example, a polynucleotide sequence encoding a reporter polypeptide can be operatively linked to a regulatory element, in which case the regulatory element confers its regulatory effect on the polynucleotide similarly to the way in which the regulatory element would effect a polynucleotide sequence with which it normally is associated with in a cell. A first polynucleotide coding sequence also can be operatively linked to a second (or more) coding sequence such that a chimeric polypeptide can be expressed from the operatively linked coding sequences. The chimeric polypeptide can be a fusion polypeptide, in which the two (or more) encoded peptides are translated into a single polypeptide (see, e.g., Example 4), i.e., are covalently bound through a peptide bond; or can be translated as two discrete peptides that, upon translation, can associate with each other to form a stable complex.

A polynucleotide such as a reporter gene can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a polypeptide, for expressing the encoded peptide in a particular cell. An expression vector can contain, for example, the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible, tissue specific, or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.* Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A polynucleotide encoding a reporter polypeptide can be operatively linked, for example, to a tissue specific regulatory element, for example, a muscle cell specific regulatory element, wherein expression of the reporter polypeptide is restricted to the muscle cells in an individual, or to muscle cells in a mixed population of cells in culture, for example, an organ culture. Muscle cell specific regulatory elements include, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci., USA* 88:5847-5851, 1991, which is incorporated herein by reference).

Viral expression vectors can be particularly useful for introducing a polynucleotide into a cell, including, if desired, into a cell in a subject. Viral vectors provide the advantage that they can infect host cells with relatively high efficiency and can infect specific cell types. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187, 1996, each of which is incorporated herein by reference).

A polynucleotide such as a reporter gene or a polynucleotide agent, which can be contained in a vector, can be introduced into a cell by any of a variety of methods (Sambrook et al., *Molecular Cloning: A laboratory manual* (Cold Spring Harbor Laboratory Press 1989); Ausubel et al., *Current Protocols in Molecular Biology* (John Wiley and Sons, Baltimore, Md. 1987, and supplements through 1995), each of which is incorporated herein by reference). Such methods include, for example, transfection, lipofection, microinjection, biolistic methods, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Where a test agent is identified as having myostatin modulating activity, the screening assay can further include a step of determining an amount by which the agent increases or decreases myostatin activation. For example, where an agent is identified that increases the proteolytic activity of the metalloprotease for the myostatin pro peptide above a baseline level of activity in a particular system, for example, in an in vitro assay using purified reagents or in vivo in a subject, the method can further include determining an amount by which the agent increases myostatin activation above the basal level. As such, different agents or panels of agents can be obtained that increase or decrease myostatin activation by a metalloprotease in a relatively defined amount. Such a method further provides a means to determine amounts of a particular agent useful for providing a desired level of myostatin activity. As such, the present invention provides agents and panels of agents that modulate metalloprotease mediated myostatin activation, such agents being useful as medicaments to modulate myostatin activation in a subject, for example, in a subject having a metabolic disorder such as muscular dystrophy, muscle wasting, obesity, or type 2 diabetes.

Accordingly, the invention provides methods of modulating metalloprotease mediated myostatin activation. As used herein, the term "modulate," when used in reference to an effect on metalloprotease mediated cleavage of myostatin pro peptide or metalloprotease mediated myostatin activation, means that the amount of pro peptide cleavage or myostatin activation either is increased or is reduced or inhibited. The terms "increase" and "reduce or inhibit" are used in reference to the effect of an agent on a baseline level of metalloprotease mediated myostatin pro peptide cleavage or myostatin activation. The baseline level of activity can be a level of cleavage or activation that is identified as occurring in an in vitro assay using purified pro peptide and metalloprotease under defined conditions, or using a biological sample such as a cell or tissue extract obtained from a subject, which can, but need not, be a normal healthy individual; or a level of cleavage or activation that occurs in vivo in a subject. The terms "reduce or inhibit" are used together herein because it is recognized that, in some cases, the level of metalloprotease mediated myostatin pro peptide cleavage or myostatin activation can be reduced below a level that can be detected by a particular assay. As such, it may not be determinable using such an assay as to whether, for example, a low level of myostatin pro peptide cleavage remains, or whether such cleavage is completely inhibited.

A method of modulating metalloprotease mediated myostatin pro peptide cleavage or myostatin activation can be performed, for example, by contacting a latent myostatin complex, which includes a myostatin pro peptide and a myostatin C-terminal fragment, particularly a C-terminal fragment dimer, with a metalloprotease that can cleave the myostatin pro peptide, and with an agent that can increase or decrease proteolytic cleavage of the pro peptide mediated by the metalloprotease. The metalloprotease can be any metalloprotease that can cleave the myostatin pro peptide, particularly when the pro peptide comprises a latent myostatin complex, including, for example, a BMP-1/TLD family member such as BMP-1, mTLD, mTLL-1, or mTLL-2. The agent can act in any way to modulate metalloprotease mediated cleavage of the myostatin pro peptide, including, for example, by increasing or decreasing the proteolytic activity of the metalloprotease, by competing with the pro peptide for the metalloprotease, by facilitating contact of the metalloprotease and a latent myostatin complex comprising the pro peptide, or by inducing a conformational change in the latent myostatin complex such that it is a less fit (or more fit) substrate for the metalloprotease.

A method of modulating metalloprotease mediated myostatin activation can be practiced with respect to any subject that expresses myostatin, including vertebrates and invertebrates. For example, the subject can be a human, mouse, cow, pig, sheep, goat, dog, cat, chicken, turkey, zebrafish, salmon, finfish, other aquatic organisms and other species. Examples of aquatic organisms include those belonging to the class *Piscina*, such as trout, char, ayu, carp, crucian carp, goldfish, roach, whitebait, eel, conger eel, sardine, flying fish, sea bass, sea bream, parrot bass, snapper, mackerel, horse mackerel, tuna, bonito, yellowtail, rockfish, fluke, sole, flounder, blowfish, filefish; those belonging to the class *Cephalopoda*, such as squid, cuttlefish, octopus; those belonging to the class *Pelecypoda*, such as clams (e.g., hardshell, Manila, Quahog, Surf, Soft-shell); cockles, mussels, periwinkles; scallops (e.g., sea, bay, calloo); conch, snails, sea cucumbers; ark shell; oysters (e.g., *C. virginica*, Gulf, New Zealand, Pacific); those belonging to the class *Gastropoda* such as turban shell, abalone (e.g. green, pink, red); and those belonging to the class *Crustacea* such as lobster, including but not limited to Spiny, Rock, and American; prawn; shrimp, including but not limited to *M rosenbergii, P. styllrolls, P. indicus, P. jeponious, P. monodon, P. vannemel, M. ensis, S. melantho, N. norvegious*, cold water shrimp; crab, including, but not limited to, Blue, rook, stone, king, queen, snow, brown, dungeness, Jonah, Mangrove, soft-shelled; squilla, krill, langostinos; crayfish/crawfish, including, but not limited, to Blue, Marron, Red Claw, Red Swamp, Soft-shelled, white; *Annelida; Chordata*, including, but not limited to, reptiles such as alligators and turtles; *Amphibia*, including frogs; and *Echinodermata*, including, but not limited to, sea urchins.

A method of modulating metalloprotease mediated myostatin activity can be performed in vitro or ex vivo using cells or a tissue in culture, a cell or tissue extract, a biological fluid such as a serum or plasma sample, or substantially purified reagents, including substantially purified metalloprotease and/or latent myostatin complex (see, for example, Thies et al., supra, 2001). Where the method is performed in vitro, the agent can be contacted with sample comprising the metalloprotease and latent myostatin complex by adding the agent to the sample, which generally is in a culture medium or other buffered solution. For example, where the method is performed using cells in culture, the agent can be added to the culture medium such that it contacts the metalloprotease and/or pro peptide, one or both of which can be present in cells in the culture or secreted into the medium. The agent can be selected such that it is soluble in the sample medium, or can be formulated to increase solubility, if desired.

A method of modulating myostatin activation also can be performed in vivo, including in a living subject, including with respect to cells or a tissue in situ in a subject. In general, such a method is performed by administering the agent to the subject and, therefore, the agent generally is formulated in a composition suitable for administration to the subject. As such, compositions containing an agent that can modulate metalloprotease mediated myostatin activation are provided, such compositions including the agent in a pharmaceutically acceptable carrier. Such compositions are useful as medicaments for treating a subject suffering from a muscular and/or metabolic disorder as disclosed herein, and are useful for administration to animals such as farm animals used for labor or as food products.

A composition for administration to a living subject generally includes the agent in a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the agent to be administered, and on the route of administration of the composition, which can be, for example, orally or parenterally such as intravenously, and by injection, intubation, or other such method known in the art. The composition also can contain one or more additional reagent, including, for example, nutrients or vitamins or, where the composition is administered for a therapeutic purpose, a diagnostic reagent or therapeutic agent relevant to the disorder being treated.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology* Vol. 1 (CRC Press, Boca Raton, Fla. 1984); Fraley, et al., *Trends Biochem. Sci.* 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful for practicing a method of the invention, and other "masked" liposomes similarly can be used, such liposomes extending the time that the therapeutic agent remains in the circulation. Cationic liposomes, for example, also can be modified with specific receptors or ligands (Morishita et al., *J. Clin. Invest.* 91:2580-2585 (1993), which is incorporated herein by reference).

The route of administration of a pharmaceutical composition containing an agent that modulates metalloprotease mediated myostatin activation will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a peptide agent can be prepared using D-amino acids, or can contain one or more domains based on peptidomimetics, which are organic molecules that mimic the structures of peptide domains; or based on a peptoid such as a vinylogous peptoid.

A composition as disclosed herein can be administered to a subject by various routes including, for example, orally or parenterally, such as intravenously, intramuscularly, subcutaneously, intraorbitally, intracapsularly, intraperitoneally, intrarectally, intracistemally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant.

The pharmaceutical composition can be formulated as an oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. It will be recognized that the amount of the pharmaceutical composition, for example, to treat obesity in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

A method of the invention can be used to increase the level of myostatin activation (i.e., above a baseline level of myostatin activation in the absence of an agent), for example, by contacting a latent myostatin complex and/or metalloprotease with an agent that increases proteolytic activity of the metalloprotease; or can be used to decrease the level of myostatin activation (below a baseline level), for example, by contacting a latent myostatin complex and/or metalloprotease with an agent that decreases metalloprotease mediated proteolytic activity of myostatin pro peptide. The agent can be one that decreases proteolytic activity of a metalloprotease that cleaves myostatin pro peptide of a latent myostatin complex, thereby reducing or inhibiting myostatin activation below a level of myostatin activation that occurs or would occur in the absence of the agent. Where such an agent is administered to a subject, the agent can result in increased muscle mass or decreased fat content or both in the subject. For example, the subject can be a human subject suffering from a muscle wasting disorder, wherein increased muscle mass can ameliorate the signs and symptoms of the disorder. Alternatively, the agent can be one that increases metalloprotease mediated proteolytic cleavage of myostatin pro peptide from a latent myostatin complex, thereby increasing myostatin activation above a level, if any, of myostatin activation that occurs or would occur in the absence of the agent. Where such an agent is administered to a subject, the agent can result in decreased muscle mass or increased fat content or both in the subject. Such a subject can be, for example, an undesirable organism such as an invasive fish species or rodents, wherein decreased muscle mass and/or increased fat content places the invasive species at a competitive disadvantage in the environment.

Accordingly, in one embodiment, the invention provides a method of increasing muscle mass or reducing the fat content or both of a subject by modulating proteolytic cleavage of a myostatin pro peptide by a metalloprotease such as a BMP-1/TLD family metalloprotease. Such a method can be performed, for example, by administering to the subject an agent that reduces or inhibits the proteolytic activity of a protease that cleaves myostatin pro peptide, thereby preventing activation of latent myostatin and increasing muscle mass in the subject. The subject in which muscle mass is to be increased can be any subject in which myostatin is expressed, particularly a vertebrate organism, including domesticated animals (e.g., a feline or canine species), farm animals or animals that are raised as a food source, including mammalian species (e.g., an ovine, porcine, or bovine species), avian species (e.g., chickens or turkeys), and piscine species (e.g., salmon, trout, or cod). For example, where such a method is performed on an organism that is useful as a food source, the protein content of the food can be increased, the cholesterol level can be decreased, and the quality of the foodstuff can be improved. Thus, a method of the invention can be performed on any eukaryotic organism that expresses myostatin and relies on metalloprotease mediated cleavage of myostatin pro peptide to activate myostatin, including a vertebrate organism, for example, mammalian, avian or piscine organism, or an invertebrate organism, for example, a mollusk, echinoderm, gastropod or cephalopod. In one embodiment, the subject is a human subject, for example, a subject suffering from a metabolic disorder such as a muscular disorder (e.g., a dystonia or dystrophy), a wasting disorder (e.g., cachexia), clinical obesity, or type 2 diabetes.

As such, the invention also provides a method for ameliorating a metabolic disorder in a subject by administering an agent that modulates metalloprotease mediated myostatin activation in the subject. As used herein, the term "ameliorate," when used in reference to a metabolic disorder, means that signs or symptoms associated with the disorder are lessened. Amelioration of the disorder can be identified using any assay generally used by the skilled clinician to monitor the particular metabolic disorder, for example, a glucose tolerance test for monitoring diabetes, or a serum leptin assay for body fat analysis (McPherron and Lee, supra, 2002). Amelioration of a metabolic disorder such as obesity or cachexia can be monitored simply by measuring the subject's body weight.

Heterozygous myostatin knock-out mice have increased skeletal muscle mass, although to a lesser extent than that observed in homozygous mutant mice, indicating that myostatin acts in a dose-dependent manner in vivo. Furthermore, overexpression of myostatin in animals has the opposite effect with respect to muscle growth. For example, nude mice carrying myostatin-expressing tumors developed a wasting syndrome characterized by a dramatic loss of muscle and fat weight, and resembling cachexia as occurs in patients with chronic diseases such as cancer or AIDS. In addition, the serum levels of myostatin immunoreactive material have been correlated with the status of patients with respect to muscle wasting (Gonzalez-Kadavid et al., supra, 1998). Thus, patients with AIDS, who also showed signs of cachexia as measured by loss of total body weight, had slightly increased serum levels of myostatin immunoreactive material compared to either normal males without AIDS or to AIDS patients that did not have weight loss. Myostatin not only affects muscle mass, but also affects the overall metabolism of an organism. For example, myostatin is expressed in adipose tissue, and myostatin deficient mice have a dramatic reduction in fat accumulation as the animals age. The overall anabolic effect on muscle tissue that results in response to decreased myostatin activity can alter the overall metabolism of the organism and affect the storage of energy in the form of fat, as demonstrated by the introduction of a myostatin mutation into an obese mouse strain (agouti lethal yellow ($A^y$) mice), which suppressed fat accumulation by five-fold. Abnormal glucose metabolism also was partially suppressed in agouti mice containing the myostatin mutation.

As such, the agents and methods of the present invention, which reduce or inhibit metalloprotease mediated myostatin activation, can be used to treat or prevent metabolic diseases such as obesity and type 2 diabetes. The methods of the invention are useful, for example, for ameliorating various metabolic disorders, including, for example, the cachexia associated with chronic diseases such as cancer (see Norton et al., *Crit. Rev. Oncol. Hematol.* 7:289-327, 1987, which is incorporated herein by reference), as well as conditions such as type 2 diabetes, obesity, and other metabolic disorders. As used herein, the term "metabolic disorder" refers to a condition that is characterized, at least in part, by an abnormal amount, development or metabolic activity of muscle and/or adipose tissue. Such metabolic disorders include, for example, obesity; muscle wasting disorders such as muscular dystrophy, neuromuscular diseases, cachexia, and anorexia; and disorders such as type 2 diabetes, which generally, but not necessarily, is associated with obesity. The term "abnormal," when used in reference to the amount, development or metabolic activity of muscle and/or adipose tissue, is used in a relative sense in comparison to an amount, development or metabolic activity that a skilled clinician or other relevant artisan would recognize as being normal or ideal. Such normal or ideal values are known to the clinician and are based on average values generally observed or desired in a healthy individual in a corresponding population. For example, the clinician would know that obesity is associated with a body weight that is about twenty percent above an "ideal" weight range for a person of a particular height and body type. However, the clinician would recognize that a body builder is not necessarily obese simply by virtue of having a body weight that is twenty percent or more above the weight expected for a person of the same height and body type in an otherwise corresponding population. Similarly, the artisan would know that a patient presenting with what appears to abnormally decreased muscle activity could be identified as having abnormal muscle development, for example, by subjecting the patient to various strength tests and comparing the results with those expected for an average healthy individual in a corresponding population.

A method for ameliorating a metabolic disorder in a subject can be performed, for example, by administering to the subject an agent that reduces or inhibits the proteolytic activity of a protease that cleaves myostatin pro peptide, thereby preventing activation of latent myostatin in the cell and ameliorating the metabolic disorder. As indicated above, the metabolic disorder can be any disorder associated with increased or undesirably high myostatin activation or activity, including, for example, a muscle wasting disorder such as is associated with muscular dystrophy, cachexia (e.g., associated with a cancer or acquired immunodeficiency disease), or sarcopenia; or a metabolic disorder such as clinical obesity or type 2 diabetes. By way of example, sarcopenia is a metabolic disorder that is characterized by a loss of skeletal muscle mass, quality, and strength, and can lead to frailty in the elderly. Examples of skeletal muscle properties that contribute to its overall quality include contractility, fiber size and type, and glucose uptake and metabolism. Sarcopenia has important consequences because the loss of lean body mass reduces function, and because a loss of approximately 40% of lean body mass generally is fatal (see, for example, Roubenoff and Castaneda, *J. Amer. Med. Assn.* 286, 2001). A method of the invention provides a means to ameliorate sarcopenia by reducing or inhibiting metalloprotease mediated myostatin activation, thereby allowing increased muscle growth and development in the subject.

The following examples are intended to illustrate but not limit the invention.

EXAMPLE 1

BMP-1/TLD Metalloprotease Family Members Cleave Myostatin Pro Peptide

This example demonstrates that the members of the bone morphogenic protein-1/Tolloid (BMP-1/TLD) family of metalloproteases cleave the myostatin pro peptide.

Five hundred ng of purified myostatin pro peptide or of purified latent myostatin complex comprising the pro peptide and C-terminal dimer (Lee and McPherron, supra, 2001) was incubated overnight at 37° C. with 100 ng purified BMP-1, mTLD, mTLL-1, or mTLL-2 (Scott et al., *Devel. Biol.* 213: 283-300, 1999, which is incorporated herein by reference). Reaction products were analyzed by sodium dodecyl sulfate-polyacrylamide gel electrophoresis (SDS-PAGE) followed by western blot analysis using antiserum raised against the myostatin pro peptide (Lee and McPherron, supra, 2001).

A discrete proteolytic cleavage product of the pro peptide was detected in each reaction containing one of the four proteases, but not in control reactions that did not contain a protease. Moreover, each of the proteases cleaved the pro peptide whether it was in a purified form or in a complex with the myostatin C-terminal dimer. These results demonstrate that the BMP-1/TLD metalloproteases cleave the myostatin pro peptide.

EXAMPLE 2

Metalloprotease Cleavage of Myostatin Pro Peptide Activates Latent Myostatin

This example demonstrates that cleavage of the myostatin pro peptide by a BMP-1/TLD metalloprotease activates latent myostatin.

Purified myostatin pro peptide and C-terminal dimer complex was incubated with mTLL-1, then examined using a reporter gene assay that specifically detects myostatin activity. A204 rhabdomyosarcoma cells were transfected with the pGL3-(CAGA)$_{12}$ luciferase reporter gene construct, which comprises the luciferase coding sequence linked to the TGF-β responsive CAGA sequence from the promoter of the TGF-β inducible PAI-1 gene (Thies et al., supra, 2001). The transfected cells were contacted with either untreated pro peptide/C-terminal dimer complex or complex that had been pre-incubated with mTLL-1. Incubation of the complex with mTLL-1 dramatically increased the amount of luciferase activity detected in the reporter cell assay, whereas no change was observed in cells treated with mTLL-1 alone or with the myostatin complex alone (FIG. 1).

Figure 2:
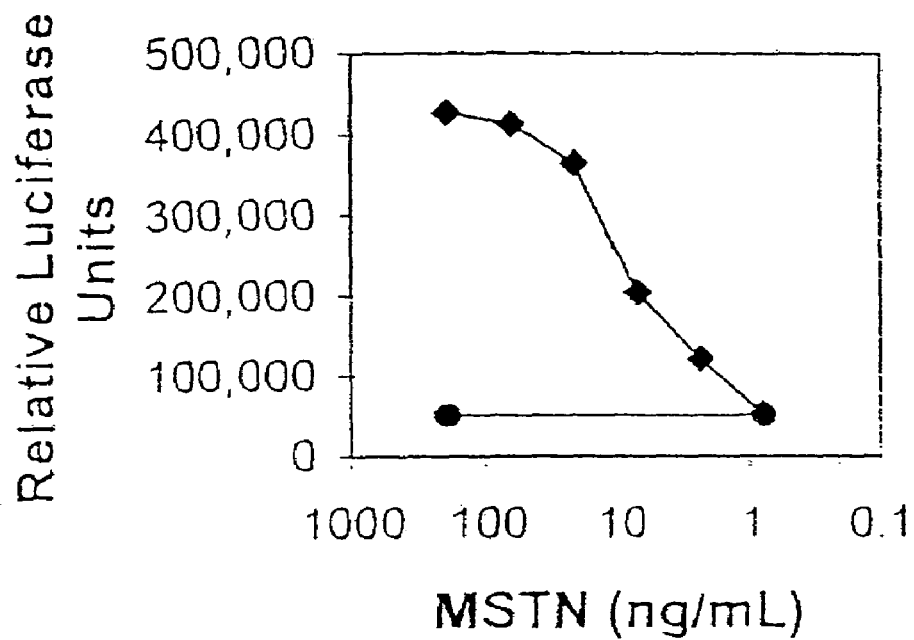
FIG. 2 shows a standard curve generated using the luciferase reporter assay, wherein the transfected cells (see FIG. 1, above) were contacted with the specified amounts of active purified C-terminal myostatin dimer (diamonds). Control luciferase activity (no myostatin) is shown by the circles.

In order to determine the extent of myostatin activation by mTLL-1, a standard curve was generated using purified myostatin C-terminal dimer in the reporter gene assay (FIG. 2), then the amount of luciferase activity in cells treated with the mTLL-1 treated complex was compared to the standard curve. A comparison of the amount of myostatin activity present in the mTLL-1-treated sample and the degree of proteolytic processing of the pro peptide by mTLL-1 in this sample revealed that at least about 50% of the proteolytically-cleaved myostatin complex was active in the reporter assay. These results demonstrate that cleavage of the myostatin pro peptide in a complex of the pro peptide and myostatin C-terminal dimer by the BMP-1/TLD metalloprotease, mTLL-1, activates myostatin.

EXAMPLE 3

Peptide Substrates for Tolloid Family Members

A series of three peptides each of 10, 20, 30, 40, or 50 amino acid residues was synthesized based on the sequence of the myostatin pro peptide, and encompassing the BMP-1/TLD metalloprotease cleavage site (amino acid residues "RD" as shown in bold, below, in wild type peptides; SEQ ID NOS:9, 12, 15, 18, and 21). Peptides in which the arginine residue at the P1 position just upstream of the cleavage site was changed to a glutamine residue (SEQ ID NOS:10, 13, 16, 19, and 22; see bold), and peptides in which the aspartic acid at the P1' position just downstream of the cleavage site was changed to an alanine (SEQ ID NOS:11, 14, 17, 20, and 23; see bold), also were synthesized. The sequences of the peptides are shown below:

```
50-mer
KDVIRQLLPKAPPLRELIDQYDVQRDDSSDGSLEDDDYHATTETIITMPT    (SEQ ID NO:9)

KDVIRQLLPKAPPLRELIDQYDVQQDDSSDGSLEDDDYHATTETIITMPT    (SEQ ID NO:10)

KDVIRQLLPKAPPLRELIDQYDVQRADSSDGSLEDDDYHATTETIITMPT    (SEQ ID NO:11)

40-mer:
QLLPKAPPLRELIDQYDVQRDDSSDGSLEDDDYHATTETI;             (SEQ ID NO:12)

QLLPKAPPLRELIDQYDVQQDDSSDGSLEDDDYHATTETI;             (SEQ ID NO:13)
and

QLLPKAPPLRELIDQYDVQRADSSDGSLEDDDYHATTETI.             (SEQ ID NO:14)

30-mer:
APPLRELIDQYDVQRDDSSDGSLEDDDYHA;                       (SEQ ID NO:15)

APPLRELIDQYDVQQDDSSDGSLEDDDYHA;                       (SEQ ID NO:16)
and
```

-continued

APPLRELIDQYDVQRADSSDGSLEDDDYHA.                       (SEQ ID NO:17)

20-mer:
ELIDQYDVQRDDSSDGSLED;                                  (SEQ ID NO:18)

ELIDQYDVQQDDSSDGSLED;                                  (SEQ ID NO:19)
and

ELIDQYDVQRADSSDGSLED.                                  (SEQ ID NO:20)

10-mer:
YDVQRDDSSD;                                            (SEQ ID NO:21)

YDVQQDDSSD;                                            (SEQ ID NO:22)
and

YDVQRADSSD.                                            (SEQ ID NO:23)

Peptides were supplied as lyophilized powders and stock solutions of 1.0 mM were prepared in 60% acetonitrile—0.1%trifluoroacetic acid (TFA) and 40% water. Activity of the enzymes on the peptide substrates was assessed by combining 70 µl of water, 20 µl of either mock conditioned medium or conditioned medium containing the protein of interest, and 10 µl of synthetic peptide. Samples were incubated overnight at either room temperature or 37° C., then reactions were quenched by reducing the pH through the addition of 1.0 µl of 0.1% TFA. Each aliquot was applied to a 2 cm C18 guard column cartridge (Supelco) and peptides were eluted using an acetonitrile gradient (0-40% over 20 minutes) in 0.1% TFA. Peaks corresponding to cleaved peptide fragments were identified and confirmed using mass spectrometry. The 40-mer, 30-mer, and 20-mer wild type and R->Q mutant peptides were cleaved by conditioned media containing TLL-2, whereas the peptides containing the D->A mutation at the P1' position were not cleaved; the 50-mer was insoluble under the conditions used, and the cleavage products of the 10-mer were difficult to detect due to their small size (i.e., 5-mers).

EXAMPLE 4

Activation of Latent Myostatin by BMP-1/Tolloid Family Metalloproteases

This example demonstrates that BMP-1/TLL family members can cleave and activate latent myostatin.

Myostatin purification and analysis. The generation of CHO cell lines overexpressing myostatin was described previously[5,6] (numbered references listed at end of Example 4). Similar strategies were used to generate CHO lines expressing mutant forms of full-length human myostatin and pro peptide/Fc fusion proteins (see U.S. Publ. No. US 2003/0104406 A1). Mutant human full-length myostatin sequences were based on SEQ ID NO:2, and the mutant pro peptide sequences were based on amino acid residues 24 to 266 of SEQ ID NO:2. Myostatin pro peptide/C-terminal dimer complexes were purified from the conditioned medium of CHO expressing cells as described[5]. Pro peptide/Fc fusion proteins were purified using a Protein A-SEPHAROSE gel column. Antibodies directed against bacterially-produced myostatin C-terminal domain and pro peptide were as described[1,5].

Proteinase and reporter gene assays. Purified BMP-1, mTLD, mTLL-1, and mTLL-2 proteinases were prepared as described[15]. Myostatin activity was measured using the pGL3-(CAGA)$_{12}$-luciferase reporter assay in A204 rhabdomyosarcoma cells as described[6]. A standard curve using purified myostatin C-terminal dimer was generated for each set of assays in order to quantify myostatin activity.

Injection of mice. Female BALB/c mice (Charles River) weighing 17 g to 19 g were injected intraperitoneally on days 1, 4, 8, 15, and 22 either with PBS alone or with various proteins diluted in PBS; doses of proteins administered were as follows: pro peptide/Fc fusion proteins—1 mg/kg or 10 mg/kg; IgG2am (control antibody)—10 mg/kg; and JA16 (myostatin neutralizing antibody)—60 mg/kg. Mice were sacrificed on day 29 for muscle analysis. Muscles from both sides of each animal were dissected and weighed; the average weight was used for each muscle.

Figure 3A:
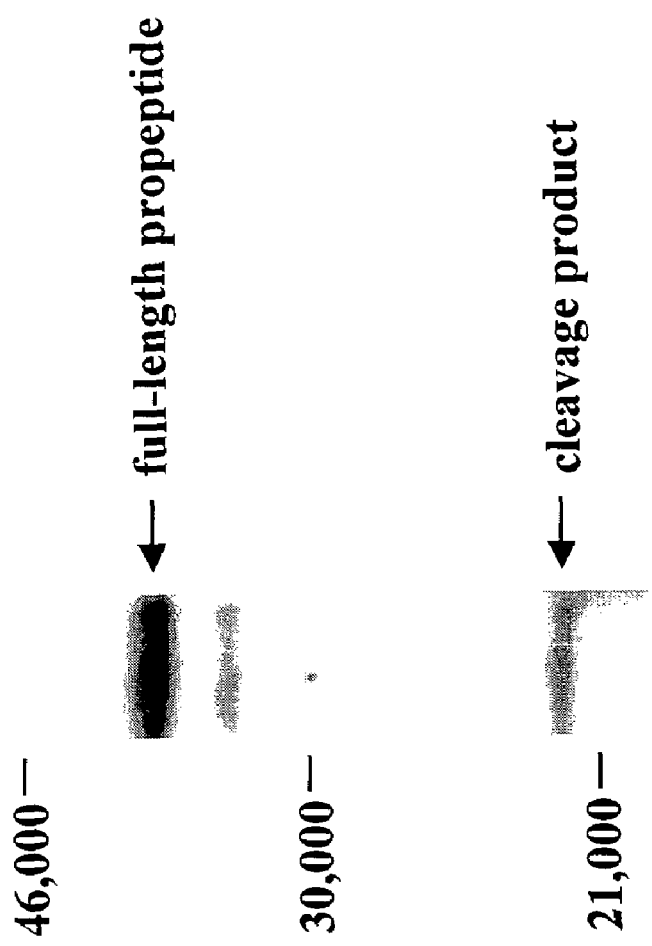
FIGS. 3A to 3E show determination of cleavage of the myostatin pro peptide by BMP-1/TLD family of proteinases.

The generation of Chinese hamster ovary (CHO) cells overexpressing myostatin has been described[5,6]. Like other TGF-β family members, myostatin produced by CHO cells is cleaved at a dibasic site to generate an N-terminal pro peptide and a disulfide-linked dimer of C-terminal fragments. In the course of characterizing the secretion of myostatin by these cells, the presence was noted of a discrete cleavage product of the pro peptide (as detected by western blot analysis using antibodies specific for the pro peptide). This cleavage product was detected in the conditioned medium of CHO cells transfected with expression constructs containing either the full-length myostatin precursor protein (not shown) or the myostatin pro peptide alone in the absence of the C-terminal domain (FIG. 3A). Because the myostatin pro peptide can maintain the C-terminal dimer in a latent state both in vitro[5,6] and in vivo[7,8], and because proteolytic cleavage of the TGF-β pro peptide is believed to be one mechanism for activating latent TGF-β[10-14], a role for cleavage of the myostatin pro peptide in regulating myostatin latency was investigated.

Figure 3B:
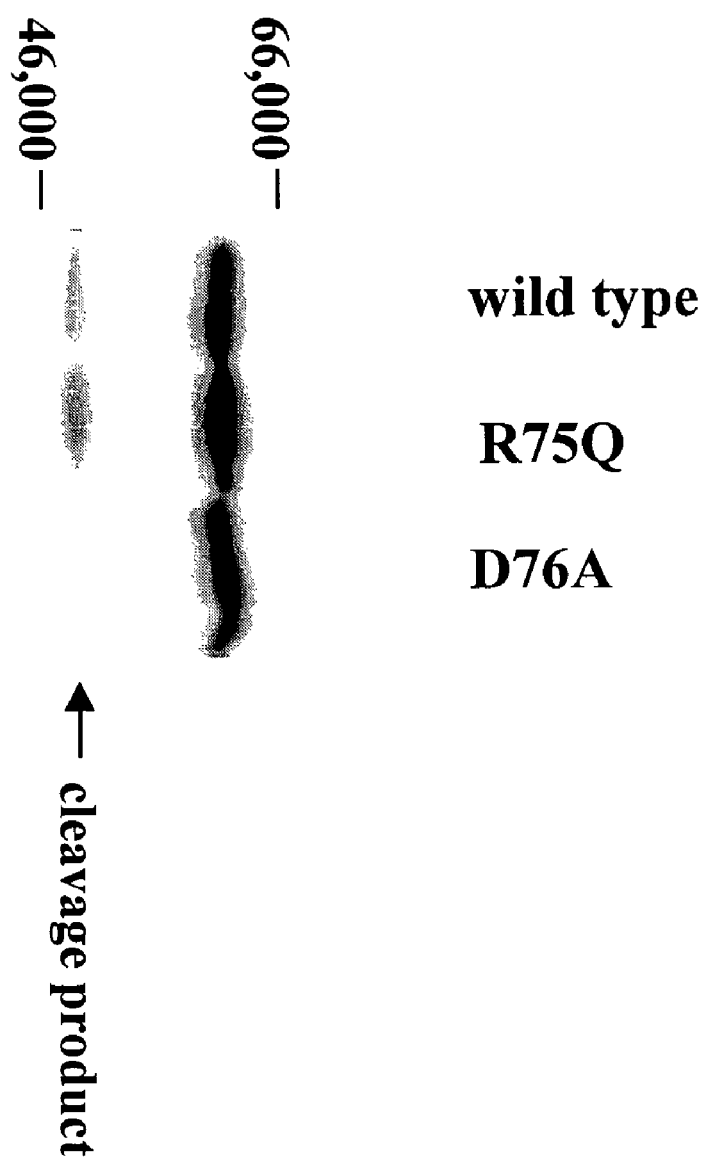

N-terminal sequencing revealed that the pro peptide degradation product detected in CHO cell conditioned medium resulted from proteolytic cleavage between arginine 75 and aspartate 76. In order to determine whether either of these amino acid residues is essential for proteolytic cleavage, CHO cell lines expressing mutant versions of the pro peptide, in which either the arginine or aspartate residue was changed to glutamine or alanine, respectively, were generated. To enhance stability of these proteins for in vivo studies (see below), the mutant pro peptides were fused with an Fc domain. Although changing the arginine to glutamine had no effect on proteolytic cleavage, no degradation product could be detected in conditioned medium prepared from CHO cells expressing the aspartate to alanine mutant pro peptide/Fc fusion protein (FIG. 3B; see, also, Example 3). The requirement for aspartate at the cleavage site suggested that members of the BMP-1/TLD family of metalloproteinases were responsible for generating this degradation product. A number of substrates have been identified for mammalian members of the BMP-1/TLD family, and in nearly every case, proteolytic cleavage has been shown to occur immediately N-terminal to an aspartate residue[15,16]. Furthermore, mutagenesis studies have documented the importance of the aspartate residue in rendering these sites susceptible to proteolytic cleavage[17]. As there were no apparent reports of other proteinases with a similar specificity or requirement for an aspartate residue just C-terminal to the scissile bond in protein substrates, the ability of members of the BMP-1/TLD family to cleave the myostatin pro peptide in vitro was investigated.

Figure 3C:
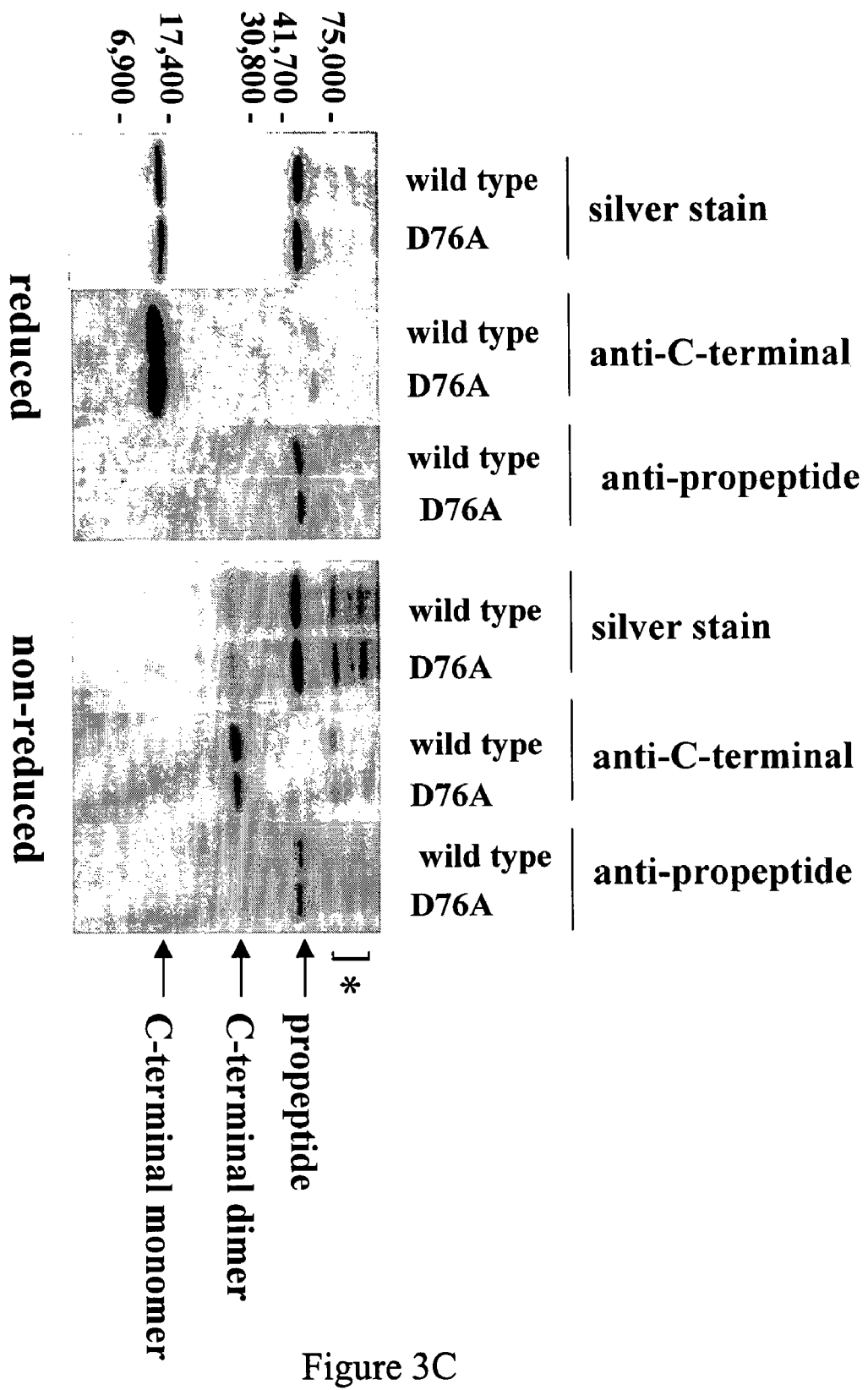
Figure 3D:
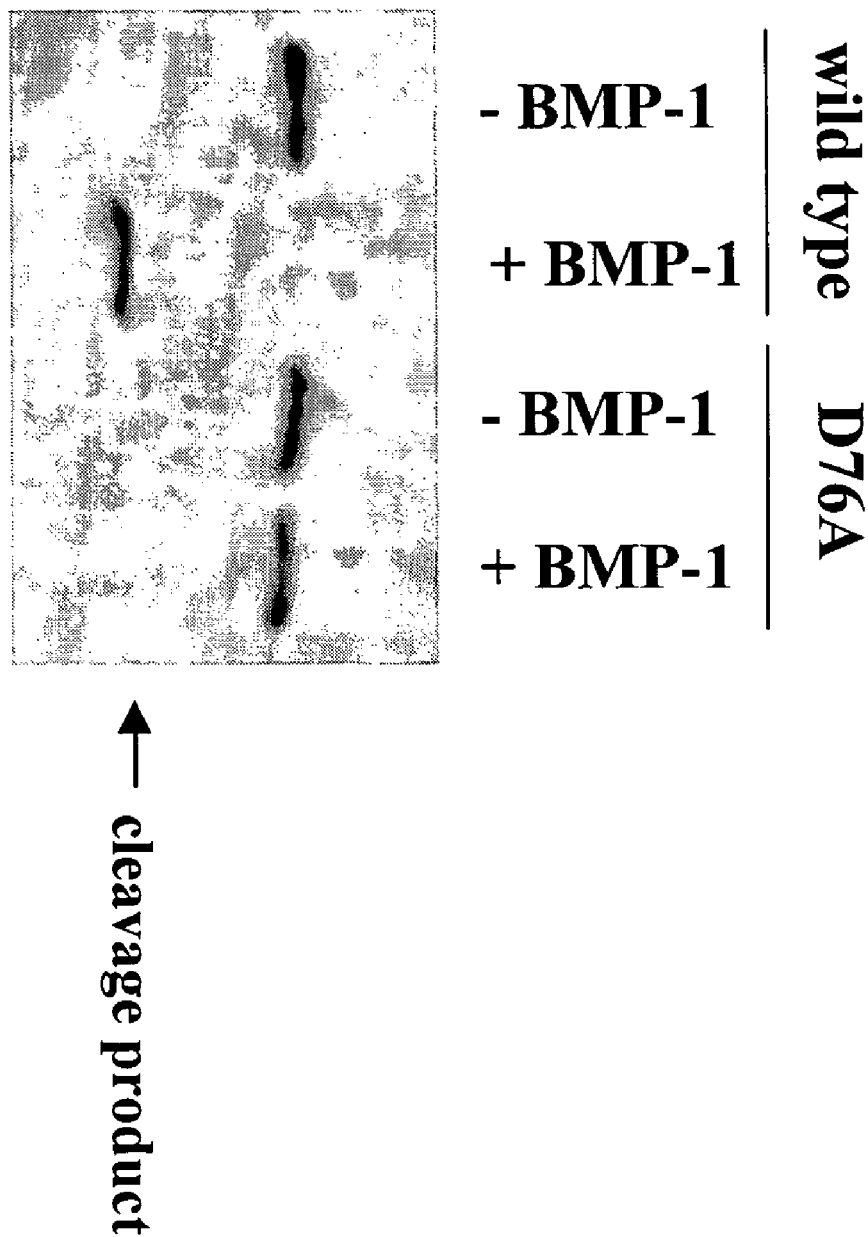

Myostatin was purified from the conditioned medium of overproducing CHO cells[5]. After successive fractionation on hydroxyapatite, lentil lectin SEPHAROSE gel, DEAE agarose, and heparin SEPHAROSE gel, a purified preparation of the myostatin latent complex was obtained that consisted of the N-terminal pro peptide bound non-covalently to the C-terminal dimer (FIG. 3C). As shown in FIG. 3D, incubation of the purified latent complex with purified BMP-1 resulted in complete cleavage of the pro peptide to generate a single product with an electrophoretic mobility identical to that detected in conditioned medium prepared from CHO cells engineered to overproduce myostatin. N-terminal sequencing of BMP-1-treated pro peptide confirmed that cleavage occurred immediately N-terminal to aspartate 76.

Figure 3E:
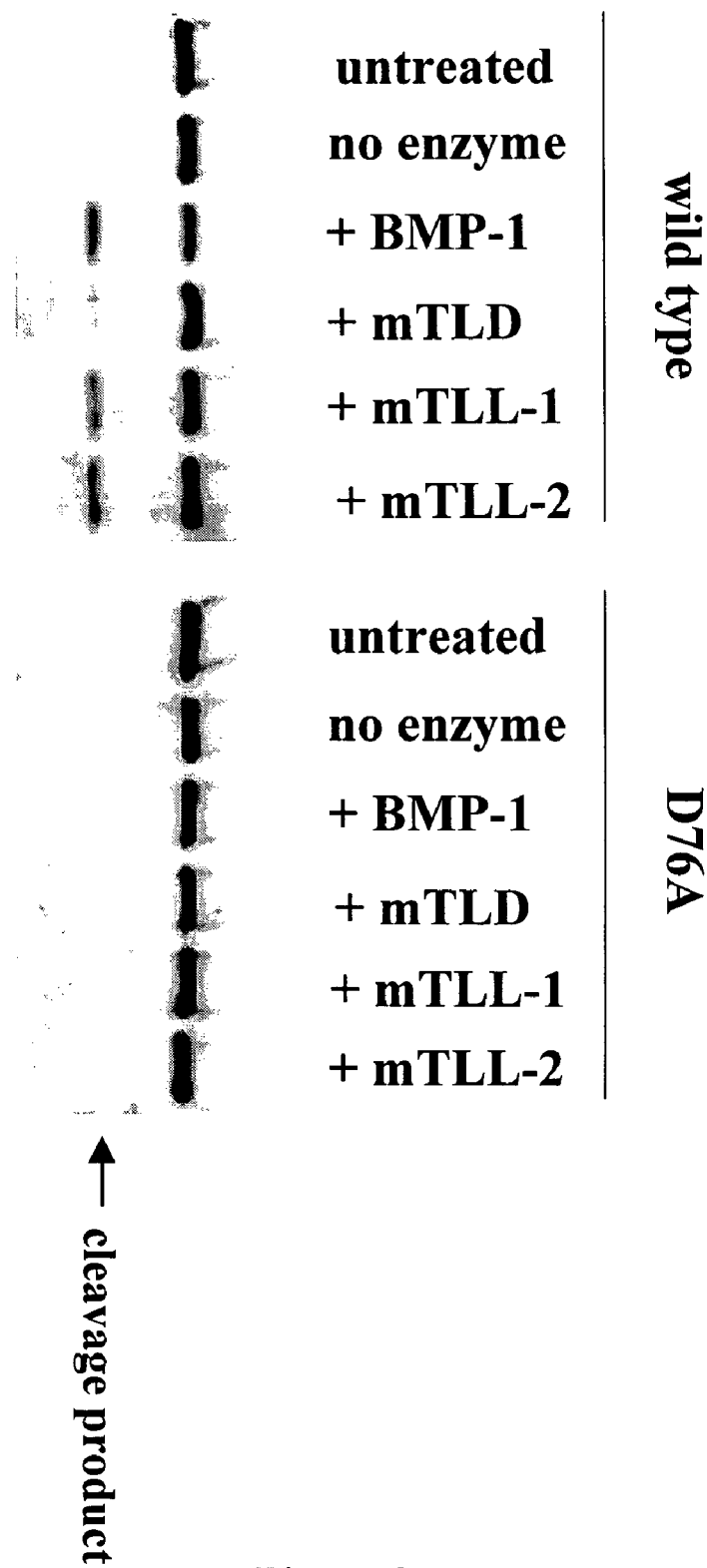

The ability of the other mammalian members of the BMP-1/TLD family, including mTLD, mTLL-1, and mTLL-2, to cleave the pro peptide also was tested. For these experiments, enzyme concentrations were used that resulted in only partial cleavage, thus allowing a comparison of the relative activities of the four enzymes. As shown in FIG. 3E, incubation of the latent complex with each of the four proteinases resulted in cleavage of the pro peptide. Three of the proteinases, BMP-1, mTLL-1, and mTLL-2, were approximately equally effective in cleaving the pro peptide, while mTLD was consistently less active than the other three, even though the same mTLD preparation was fully active against known substrates such as procollagen. All four of these proteinases also cleaved pro peptide that had been purified away from the C-terminal dimer.

Figure 4A:
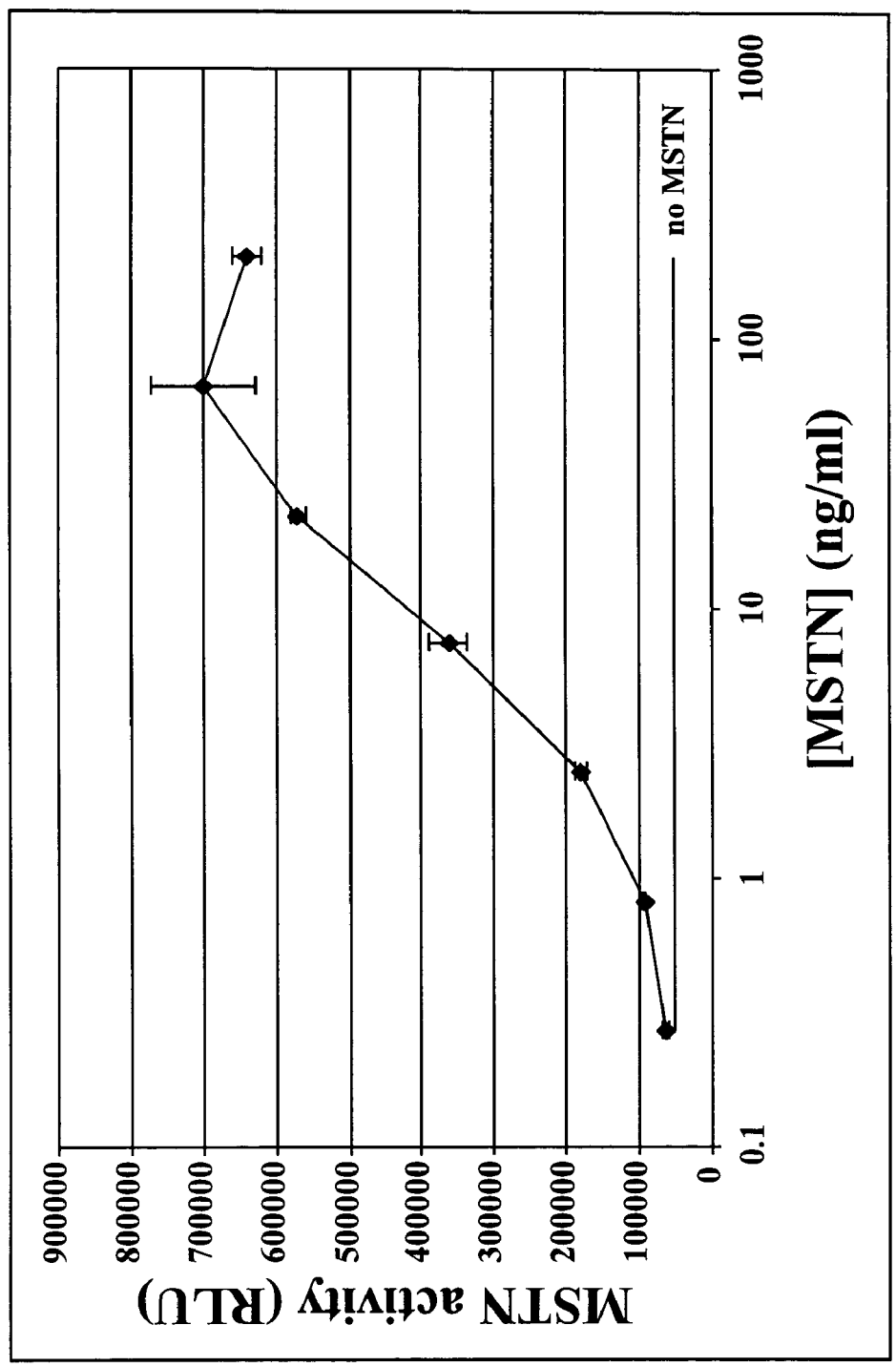
FIGS. 4A to 4D show activation of latent myostatin activity by BMP-1/TLD proteinases.
Figure 4B:
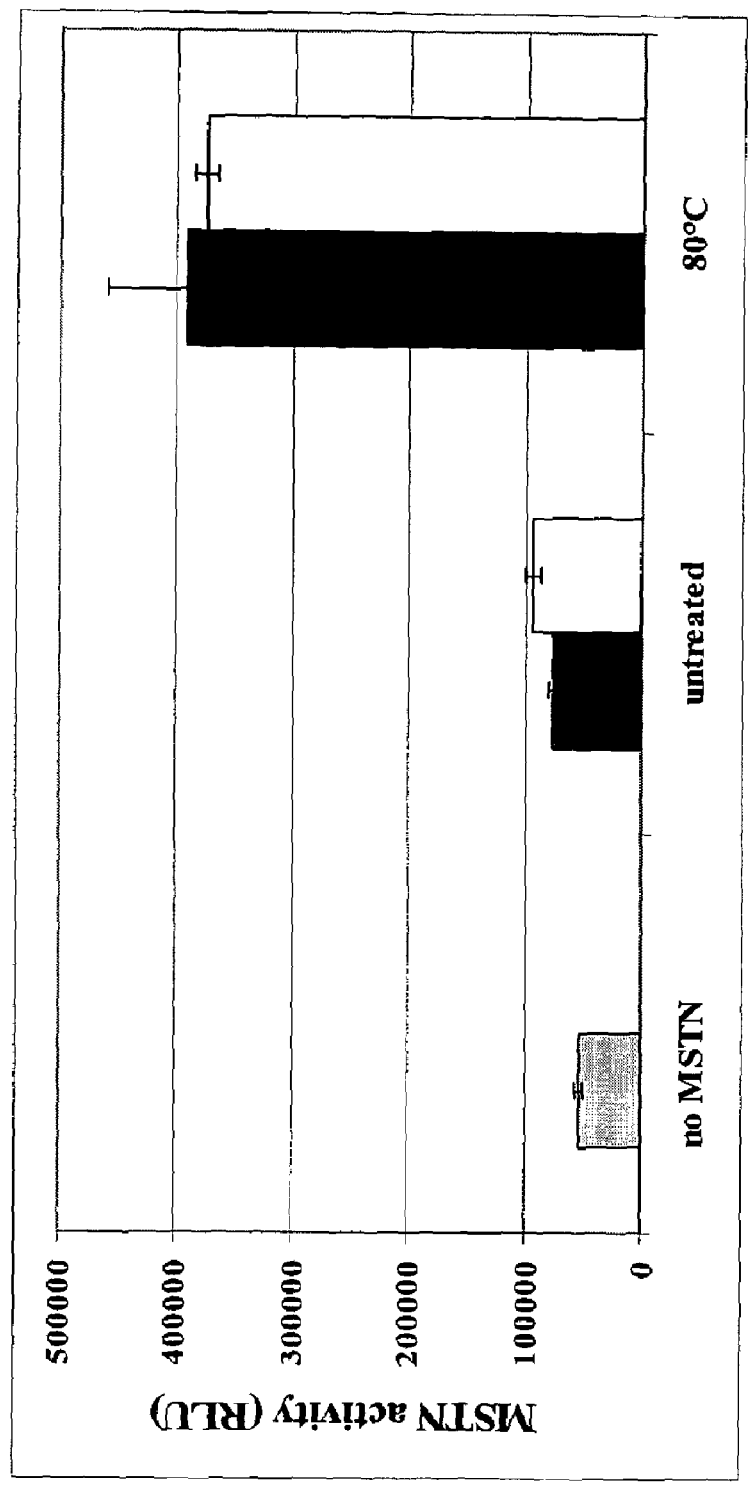
Figure 4C:
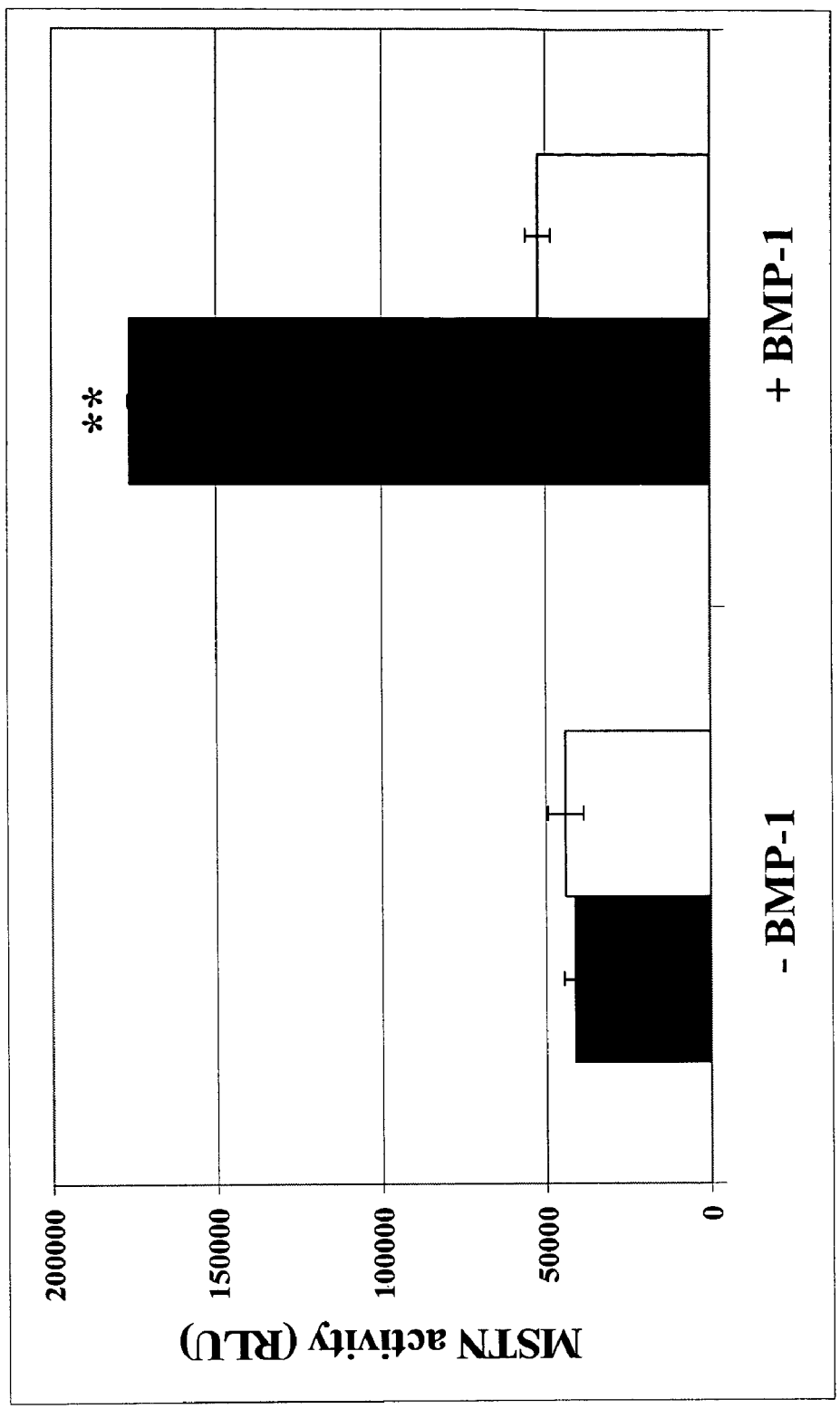
Figure 4D:
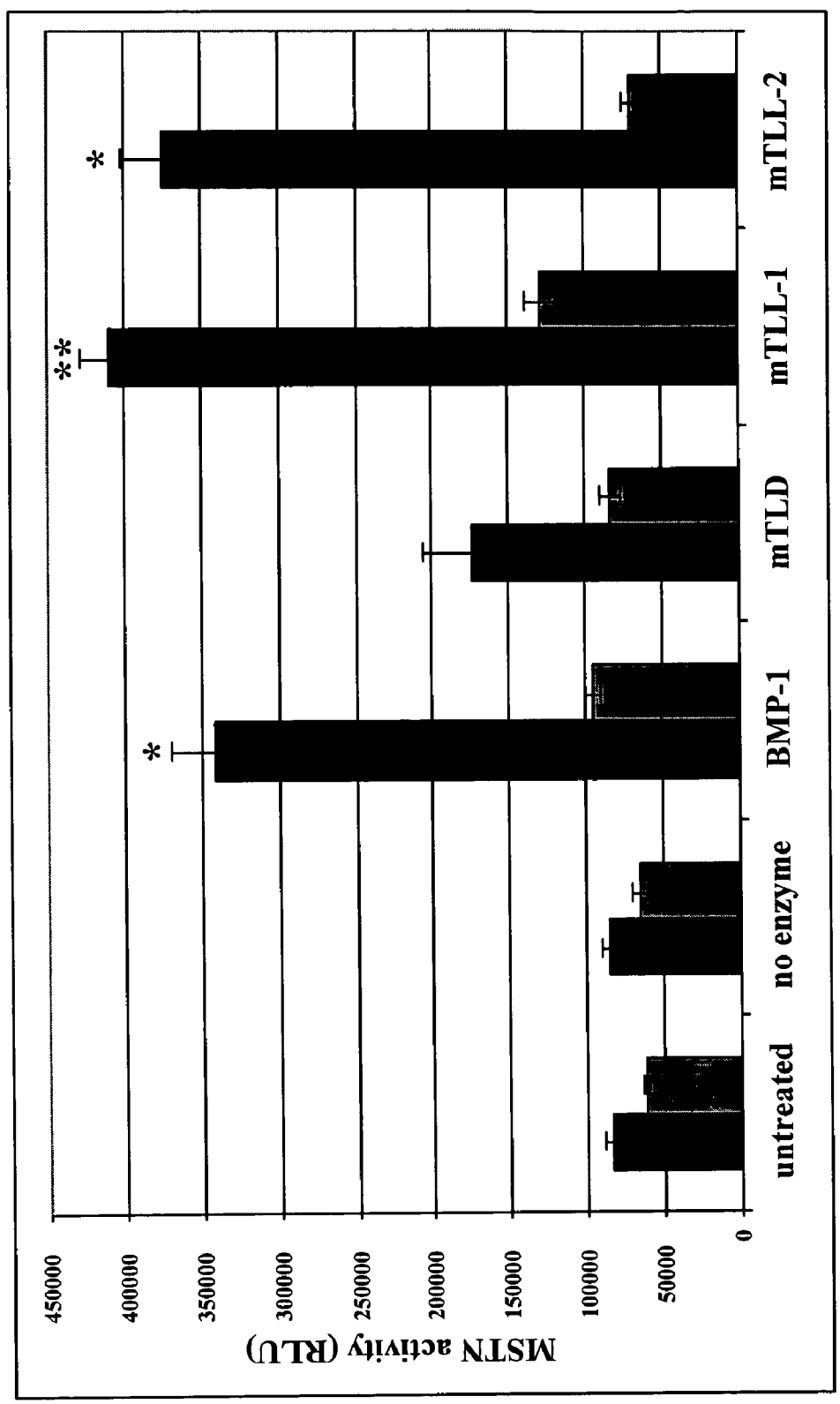

In order to determine the effect of proteolytic cleavage of the pro peptide on myostatin latency, myostatin biological activity was measured in latent complexes treated with each of the four proteinases. For this purpose, a reporter gene assay was used in which A204 rhabdomyosarcoma cells were transfected with the pGL3-(CAGA)$_{12}$-luciferase construct and incubated with myostatin[6]. As described previously, the addition of purified myostatin C-terminal dimer to these cells resulted in an increase in luciferase activity above basal levels (FIG. 4A). In contrast, purified myostatin latent complex was inactive in this assay, but could be activated by incubation at 80° C. for 5 minutes (FIG. 4B). As shown in FIG. 4C, the latent complex was also activated by pretreatment with BMP-1. Based on quantification of myostatin activity relative to a standard curve, cleavage of the pro peptide by BMP-1 was approximately as effective as heat treatment in activating the latent complex. The latent complex was also activated by pretreatment with the other proteinases, and the extent of activation correlated roughly with the extent of proteolytic cleavage by these enzymes (FIG. 4D).

The requirement for aspartate at the cleavage site also was examined. A CHO cell line expressing high levels of a mutant form of myostatin, in which aspartate 76 was changed to alanine, was generated and the latent complex was purified from the conditioned medium of these cells. As shown in FIG. 3C, the mutation had no effect on the ability of the pro peptide to bind to the C-terminal dimer; the mutant pro peptide and C-terminal dimer remained tightly associated throughout the purification. Moreover, the mutant pro peptide maintained the complex in a latent form that could be activated by heating, as assessed by the luciferase reporter assay (FIG. 4B). However, the mutant pro peptide in the latent complex was completely resistant to proteolysis by each of the four proteinases, BMP-1, mTLD, mTLL-1, and mTLL-2 (FIGS. 3D and E), and was resistant to activation by these proteinases (FIGS. 4C and 4D).

Figure 5:
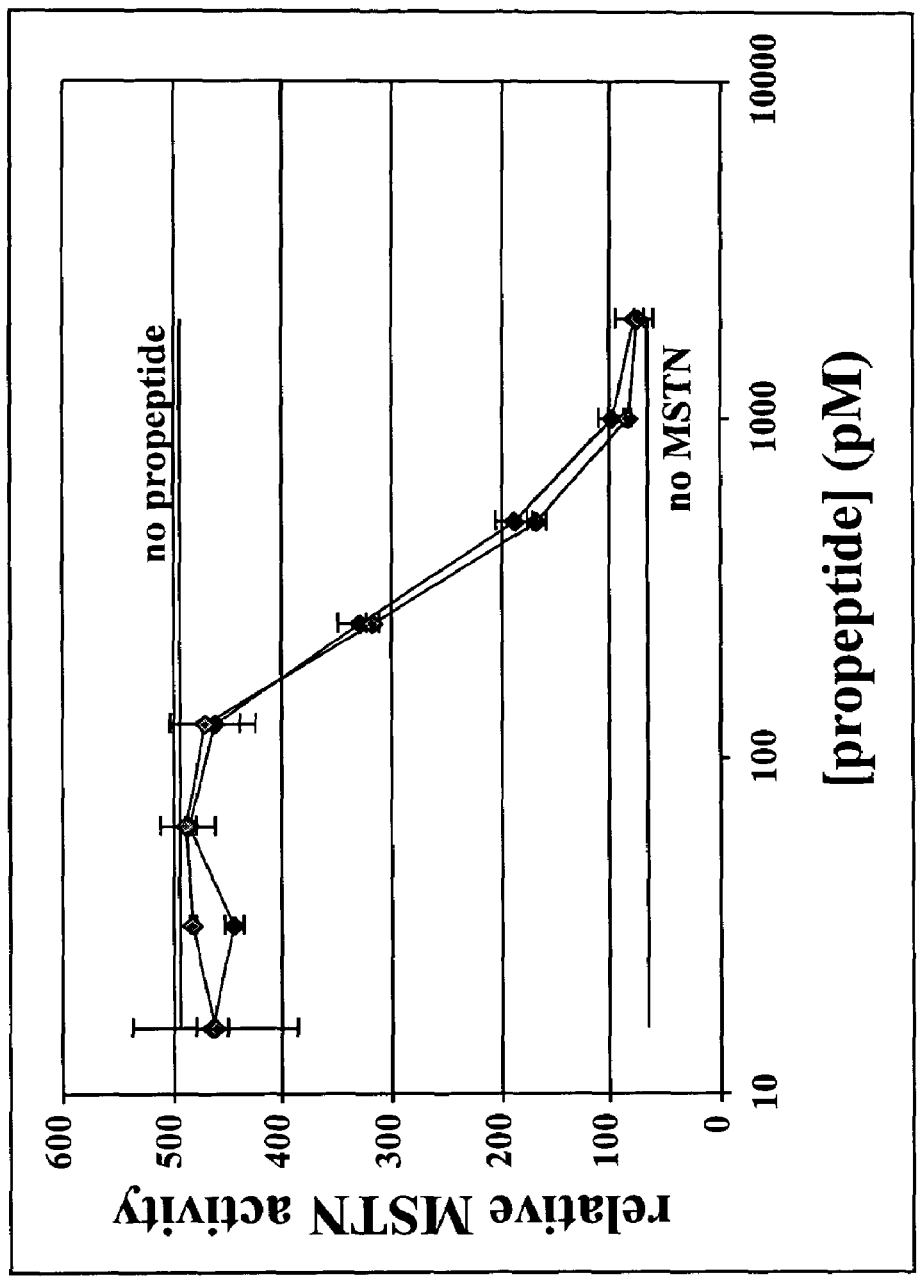
FIG. 5 shows inhibition of reporter gene activity by wild type and mutant pro peptide/Fc fusion proteins in vitro. A204 cells transfected with the reporter construct were incubated with 10 ng/ml of purified myostatin C-terminal dimer and various concentrations of wild type (dark) or D76A mutant (light) pro peptide/Fc fusion protein. Note that the wild type and mutant proteins were equally effective in blocking myostatin activity.

Finally, the role of proteolytic cleavage of the pro peptide in vivo was investigated by examining the effect of injecting wild type and mutant versions of the pro peptide into mice. As determined in previous experiments, the half-life of wild type pro peptide after intraperitoneal injections into mice could be increased from approximately 2 hours to 5 to 7 days by fusing the pro peptide to an Fc domain. For this reason, CHO cell lines expressing wild type or mutant (aspartate 76 to alanine) pro peptide fused to an Fc domain were generated, and the fusion proteins were purified using a Protein A SEPHAROSE gel column. The aspartate to alanine mutation did not affect the activity of the pro peptide in vitro, as the purified wild type and mutant pro peptide/Fc fusion proteins were equally effective in inhibiting the activity of the purified myostatin C-terminal dimer in the reporter gene assay (FIG. 5).

In order to assess the activities of these proteins in vivo, adult mice were given weekly injections of purified wild type or mutant pro peptide/Fc fusion proteins and sacrificed after four weeks for muscle analysis. For comparison, a set of mice also was injected with the JA16 myostatin neutralizing monoclonal antibody, which causes an approximately 25-30% increase in muscle mass after 12 weeks of treatment[18]. As shown in Table 1 (below), injection of wild type pro peptide/Fc fusion protein had no effect on muscle mass at doses of 1 and 10 mg/kg/week. Similarly, little or no effect was seen following injection of the aspartate to alanine mutant pro peptide/Fc fusion protein at a dose of 1 mg/kg/week. However, injection of the mutant pro peptide/Fc fusion protein at 10 mg/kg/week led to a statistically significant ($p<0.0001$) increase of 18-27% in the weight of each skeletal muscle examined. This magnitude of increase in muscle weights observed at the higher dose of the mutant pro peptide/Fc fusion protein was approximately twice that seen following injection of the JA16 myostatin neutralizing monoclonal antibody, which resulted in muscle weight increases of 10-16%.

These results demonstrate that members of the BMP-1/TLD family of metalloproteinases cleave myostatin pro peptide bound to the C-terminal dimer and activate the latent complex. Furthermore, a mutant form of the pro peptide that was resistant to cleavage by BMP-1/TLD proteinases caused increases in muscle mass when injected into adult mice, presumably by forming latent complexes incapable of being activated by this group of proteinases. This general mechanism for regulating the activity of the C-terminal dimer has been described for certain other TGF-β family members. In the case of TGF-β proteolytic cleavage of its associated pro peptide by plasmin[10,11] or by matrix metalloproteinases[12-14] is believed to be one mechanism for activating latency in vivo. In the case of the BMPs, members of the BMP-1/TLD family appear to play an important role in regulating the activity of the C-terminal dimer by cleaving and inactivating the BMP antagonist chordin[15,19-22].

All four mammalian proteinases in the BMP-1/TLD family can cleave the myostatin pro peptide in vitro, and one or more can be involved in regulating myostatin activity in vivo. In this regard, mTLL-2, unlike the other three proteinases, is expressed specifically in skeletal muscle during embryonic development[15]. The identification of the specific proteinase or proteinases involved in regulating myostatin latency will provide targets for identifying agents useful for modulating muscle mass, and will allow targeting of these enzymes for the development of novel muscle enhancing agents for both human therapeutic and agricultural applications.

TABLE 1

|  | pectoralis | triceps | quadriceps | gastrocnemius | tibialis |
|---|---|---|---|---|---|
| PBS (n = 10) | 82.8 ± 2.8 | 85.5 ± 1.6 | 142.0 ± 2.6 | 95.5 ± 1.5 | 32.6 ± 0.8 |
| IgG2am (10 mg/kg, n = 10) | 87.7 ± 1.9 | 87.8 ± 1.6 | 148.4 ± 2.3 | 98.7 ± 2.1 | 33.8 ± 0.9 |
| wild type (1 mg/kg, n = 10) | 84.3 ± 1.6 | 85.3 ± 1.8 | 145.7 ± 2.2 | 96.0 ± 1.4 | 33.2 ± 0.4 |
| D76A (1 mg/kg, n = 9) | 89.4 ± 3.5 | 90.0 ± 2.0 | 150.7 ± 2.9$^a$ | 97.7 ± 2.2 | 34.1 ± 0.6 |
| wild type (10 mg/kg, n = 10) | 87.5 ± 3.4 | 88.5 ± 2.7 | 147.1 ± 4.0 | 98.2 ± 2.2 | 33.3 ± 0.8 |
| D76A (10 mg/kg, n = 10) | 105.1 ± 1.2$^{b,c}$ | 102.1 ± 1.2$^{b,d}$ | 175.6 ± 1.2$^{b,e}$ | 112.6 ± 1.1$^{b,d}$ | 40.3 ± 1.2$^{b,d}$ |
| JA16 (60 mg/kg, n = 10) | 96.0 ± 1.2$^f$ | 94.8 ± 1.1$^f$ | 160.3 ± 1.1$^b$ | 104.9 ± 1.1$^f$ | 37.5 ± 1.1$^f$ |

$^a$ p < 0.05 (vs. PBS)
$^b$ p < 0.0001 (vs. PBS)
$^c$ p < 0.05 (vs. JA16)
$^d$ p < 0.01 (vs. JA16)
$^e$ p < 0.001 (vs. JA16)
$^f$ p < 0.001 (vs. PBS)

Each of the following publications is incorporated herein by reference:

1. McPherron, A. C., Lawler, A. M. & Lee, S.-J. Regulation of skeletal muscle mass in mice by a new TGF-β superfamily member. *Nature* 387, 83-90 (1997).
2. Bogdanovich, S. et al. Functional improvement of dystrophic muscle by myostatin blockade. *Nature* 420, 418-421 (2002).
3. Wagner, K. R., McPherron, A. C., Winik, N. & Lee, S.-J. Loss of myostatin attenuates severity of muscular dystrophy in mdr mice. *Ann Neurol* 52, 832-836 (2002).
4. McPherron, A. C. & Lee, S.-J. Suppression of body fat accumulation in myostatin-deficient mice. *J Clin Invest* 109, 595-601 (2002).
5. Lee, S.-J. & McPherron, A. Regulation of myostatin activity and muscle growth. *Proc Natl Acad Sci USA* 98, 9306-9311 (2001).
6. Thies, R. et al. GDF-8 propeptide binds to GDF-8 and antagonizes biological activity by inhibiting GDF-8 receptor binding. *Growth Factors* 18, 251-259 (2001).
7. Zimmers, T. et al. Induction of cachexia in mice by systemically administered myostatin. *Science* 296, 1486-1488 (2002).
8. Hill, J. J. et al. The myostatin propeptide and the follistatin-related gene are inhibitory binding proteins of myostatin in normal serum. *J Biol Chem* 277, 40735-40741 (2002).
9. Hill, J. J., Qiu, Y., Hewick, R. M. & Wolfman, N. M. Regulation of myostatin in vivo by GASP-1: a novel protein with protease inhibitor and follistatin domains. *Mol Endocrin* 17, 1144-1154 (2003).
10. Lyons, R. M., Keski-Oja, J. & Moses, H. L. Proteolytic activation of latent transforming growth factor-3 from fibroblast-conditioned medium. *J. Cell Biol.* 106, 1659-1665 (1988).
11. Sato, E. & Rifkin, D. Inhibition of endothelial cell movement by pericytes and smooth muscle cells: activation of a latent transforming growth factor-β1-like molecule by plasmin during co-culture. *J Cell Biol* 109, 309-315 (1989).
12. Yu, Q. & Stamenkovic, 1. Cell surface-localized matrix metalloproteinase-9 proteolytically activates TGF-β and promotes tumor invasion and angiogenesis. *Genes Dev* 14, 163-176 (2000).
13. D'Angelo, M., Billings, P., Pacifici, M., Leboy, P. & Thorsten, K. Authentic matrix vesicles contain active metalloproteases (MMP). *J Biol Chem* 276, 11347-11353 (2001).
14. Maeda, S., Dean, D., Gay, I., Schwartz, Z. & Boyan, B. Activation of latent transforming growth factor β1 by stromelysin 1 in extracts of growth plate chondrocyte-derived matrix vesicles. *J Bone Min Res* 16, 1281-1290 (2001).
15. Scott, I. et al. Mammalian BMP-1/Tolloid-related metalloproteinases, including novel family member mammalian Tolloid-like 2, have differential enzymatic activities and distributions of expression relevant to patterning and skeletogenesis. *Dev Biol* 213, 283-300 (1999).
16. Scott, I. C. et al. Bone morphogenetic protein-1 processes probiglycan. *J Biol Chem* 275, 30504-30511 (2000).
17. Lee, S.-T., Kessler, E. & Greenspan, D. S. Analysis of site-directed mutations in human pro-a2(I) collagen which block cleavage by the C-proteinase. *J Biol Chem* 265, 21992-21996 (1990).
18. Whittemore, L.-A. et al. Inhibition of myostatin in adult mice increases skeletal muscle mass and strength. *BBRC* 300, 965-971 (2003).
19. Blader, P., Rastegar, S., Fischer, N. & Strahle, U. Cleavage of the BMP-4 antagonist chordin by zebrafish tolloid. *Science* 278, 1937-1940 (1997).
20. Piccolo, S. et al. Cleavage of chordin by Xolloid metalloprotease suggests a role for proteolytic processing in the regulation of Spemann organizer activity. *Cell* 91, 407-416 (1997).
21. Marques, G. et al. Production of a DPP activity gradient in the early Drosophila embryo through the opposing actions of the SOG and TLD proteins. *Cell* 91, 417-426 (1997).
22. Pappano, W., Steiglitz, B., Scott, I. C., Keene, D. R. & Greenspan, D. S. Use of *Bmp*1/Tll1 doubly homozygous null mice and proteomics to identify and validate in vivo substrates of BMP-1 tolloid-like metalloproteinases. *Mol Cell Biol* 23, 4428-4438 (2003).

Although the invention has been described with reference to the above examples, it will be understood that modifications and variations are encompassed within the spirit and scope of the invention. Accordingly, the invention is limited only by the following claims.

What is claimed is:

1. A method of modulating myostatin activation, comprising contacting a latent myostatin complex comprising a myostatin pro-peptide and a myostatin C-terminal fragment, and a metalloprotease that can cleave the myostatin pro-peptide, wherein the metalloprotease is mammalian bone morphogenic protein-1 (BMP-1), with an agent that increases or decreases proteolytic cleavage of the pro-peptide by the metalloprotease, wherein the myostatin complex comprises SEQ ID NO: 2, SEQ ID NO: 4, SEQ ID NO: 6 or SEQ ID NO: wherein the agent is a peptide consisting of SEQ ID NO: 9-23, thereby modulating myostatin activation.

2. The method of claim 1, wherein said contacting is performed on a sample in vitro.

3. The method of claim 2, wherein the sample comprises a cell sample, a tissue sample, or a biological fluid sample.

4. The method of claim 1, wherein said contacting is performed in vivo, said method comprising administering the agent to a mammalian subject.

5. The method of claim 4, wherein the agent decreases proteolytic cleavage of the pro-peptide by the metalloprotease, thereby reducing or inhibiting myostatin activation.

6. The method of claim 5, wherein, in the subject, muscle mass is increased, fat content is decreased, or a combination thereof.

7. The method of claim 6, wherein the mammalian subject is an animal raised as a food source.

8. The method of claim 4, wherein the mammalian subject is an ovine species, a porcine species, or a bovine species.

9. The method of claim 4, wherein the mammalian subject is a human subject.

* * * * *

UNITED STATES PATENT AND TRADEMARK OFFICE
CERTIFICATE OF CORRECTION

| | | |
|---|---|---|
| PATENT NO. | : 7,572,599 B2 | Page 1 of 1 |
| APPLICATION NO. | : 10/665374 | |
| DATED | : August 11, 2009 | |
| INVENTOR(S) | : Se-Jin Lee et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 268 days.

should read (*) Notice: Subject to any disclaimer, the term of this patent is extended or adjusted under 35 U.S.C. 154(b) by 675 days.

Column 59, lines 33-43, claim 1 should read

"1. A method of modulating myostatin activation, comprising contacting a latent myostatin complex comprising a myostatin pro-peptide and a myostatin C terminal fragment, and a metalloprotease that can cleave the myostatin pro-peptide, wherein the metalloprotease is mammalian bone morphogenic protein-1 (BMP-1), with an agent that increases or decreases proteolytic cleavage of the pro-peptide by the metalloprotease, wherein the myostatin complex comprises SEQ ID NO: 2, SEQ ID NO: 4, SEQ ID NO: 6 or SEQ ID NO: 8, and wherein the agent is a peptide consisting of SEQ ID NO: 9, thereby modulating myostatin activation."

Signed and Sealed this

Twenty-ninth Day of June, 2010

David J. Kappos
*Director of the United States Patent and Trademark Office*

UNITED STATES PATENT AND TRADEMARK OFFICE
CERTIFICATE OF CORRECTION

PATENT NO.       : 7,572,599 B2                                    Page 1 of 1
APPLICATION NO.  : 10/665374
DATED            : August 11, 2009
INVENTOR(S)      : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this

Seventh Day of September, 2010

David J. Kappos
*Director of the United States Patent and Trademark Office*